United States Patent [19]
Unger et al.

[11] Patent Number: 5,407,657
[45] Date of Patent: Apr. 18, 1995

[54] HYBRID MAGNETIC RESONANCE CONTRAST AGENTS

[76] Inventors: Evan C. Unger, 13365 E. Camino La Cebadilla, Tucson, Ariz. 85749; GuanLi Wu, 2601 W. Aiden St., Tucson, Ariz. 85745

[21] Appl. No.: 202,807

[22] Filed: Feb. 28, 1994

Related U.S. Application Data

[63] Continuation-in-part of Ser. No. 949,691, Sep. 22, 1992.

[51] Int. Cl.$^6$ .......................... A61K 49/00; A61B 6/00; C08F 20/00
[52] U.S. Cl. .......................... 424/9; 528/272; 528/274; 528/275; 528/277; 528/278; 528/280; 528/289; 528/290; 528/293; 528/295; 528/296; 528/298; 528/299; 528/300; 528/302; 528/307; 528/308; 528/332; 528/335; 528/342; 528/350; 528/354; 525/437; 525/443; 525/444; 128/653.2; 128/653.4; 436/173; 436/806; 600/12
[58] Field of Search .................. 424/9; 528/272, 274, 528/275, 277, 278, 280, 289, 290, 293, 295, 296, 298, 299, 300, 302, 307, 308, 332, 335, 342, 350, 354; 525/437, 443, 444; 128/653.2, 653.4; 436/173, 806; 600/12

[56] References Cited

U.S. PATENT DOCUMENTS

| | | | |
|---|---|---|---|
| 4,822,594 | 4/1989 | Gibby | 424/9 |
| 4,834,964 | 5/1989 | Rosen | 424/9 |
| 4,863,717 | 9/1989 | Keana | 424/9 |
| 4,933,441 | 6/1990 | Gibby | 536/112 |
| 5,104,641 | 4/1992 | Rosen | 424/9 |
| 5,135,737 | 8/1992 | Keana | 424/9 |

*Primary Examiner*—Samuel A. Acquah
*Attorney, Agent, or Firm*—Antonio R. Durando; Harry M. Weiss

[57] ABSTRACT

Novel MRI contrast agents that comprise one or more metal-ion chelates in juxtaposition with one or more free-radical nitroxide compounds in a polymeric or oligomeric molecule. Both the chelate units and the free radical units may, independently, be inside the main chain of the polymer or in a side chain of the linkage portion of the polymer. The number of combined units of chelates and free radicals in the polymer or oligomer is at least two.

87 Claims, No Drawings

HYBRID MAGNETIC RESONANCE CONTRAST AGENTS

RELATED APPLICATIONS

This application is a continuation-in-part of U.S. application Ser. No. 07/949,691, filed Sep. 22, 1992, currently copending. The joint inventors of the present application are the same joint inventors of the parent application. Both applications have been assigned to the same assignee.

BACKGROUND OF THE INVENTION

1. Field of the Invention

This invention pertains to the general field of magnetic resonance contrast agents used for medical diagnostic and therapeutic applications. In particular, the invention relates to the utilization of synthetic copolymeric compounds in novel hybrid configurations comprising metal ions in conjunction with nitroxide compounds.

2. Background of the Invention

Nuclear magnetic resonance imaging (generally referred to as NMR or MRI) is based, among other factors, on the detection of spatial variations in the T1 and T2 relaxation times in the tissues under observation. Therefore, contrast agents have been developed for imaging purposes to increase the natural relaxivity of tissues (i.e, to decrease T1 and T2) at the sites of interest.

High relaxivity is desirable for several reasons. Because the contrast effectiveness of contrast agents is proportional in large part to relaxivity, an agent with much greater relaxivity can be administered in much lower dosages, thus reducing the overall toxicity to which a patient is exposed during MRI. Furthermore, extremely high relaxivity agents make it possible to design targeted agents (such as antibodies) labeled with ultra-high relaxivity contrast agents.

The prior art describes many compounds containing paramagnetic metal ions (such as gadolinium and manganese, for example) utilized as contrast agents in various chemical formulations. Such agents' relaxivity has been found to be proportional to the unpaired electrons in the metal ions, as well as being affected by water exchange and electron and rotational correlation times. Because these metal ions tend to be toxic, they need to be chelated with a ligand in order to reduce the body tissue's ability to absorb them. Contrast agents are thus created, for example, by combining diethylenetriamine pentaacetic acid (DTPA) with gadolinium and ethylenediamine tetraacetic acid (EDTA) with manganese. Unfortunately, though, as a result of the metal ion's combination with a ligand, the relaxivity of the metal ion is decreased significantly, thus also reducing its effectiveness as a contrast agent. As shown in the examples of Table 1, at least one of the relaxation parameters of metal ions generally decreases substantially when the ions are chelated.

TABLE 1

| Relaxivity of Metal Ions versus Chelates | | |
|---|---|---|
| Contrast Agent | R1 | R2 |
| $FeCl_3$ | 0.94 ± 0.06 | 1.14 ± 0.12 |
| Fe-DTPA | 0.7 | ≧0.7* |
| $MnCl_2$ | 8.73 ± 0.52 | 39.45 ± 0.52 |
| Mn-DPDP | 2.8 | 3.7 |
| Mn-EDTA-MEA | 3.29 + 0.14 | 5.76 ± 0.13 |

TABLE 1-continued

| Relaxivity of Metal Ions versus Chelates | | |
|---|---|---|
| Contrast Agent | R1 | R2 |
| $GdCl_3$ | 8.1 | ≧8.1* |
| Gd-DTPA | 4.33 ± 0.15 | 5.19 ± 0.10 |

*R2 is always greater than or equal to R1
(Measurements were taken using 0.5 Tesla and 20 MHz.)

It is known that the relaxivity of metal-ion chelates may be increased by attaching the chelates to macromolecules such as albumin or dextran, as shown by Gibby in U.S. Pat. No. 4,822,594 (1989). In theory, the polymeric macromolecules should increase the correlation time of the molecule resulting in a decrease of T1 and, possibly, of T2, which would enhance NMR imaging. In practice, though, such improvements in relaxivity are relatively modest.

Another class of well-known contrast agents consists of compounds that comprise nitroxide free radicals as the paramagnetic material used to improve the relaxivity for MRI purposes. Inasmuch as nitroxide free radicals are metabolically reduced and converted to diamagnetic material in the body, their concentration rapidly decreases below useful levels for relaxation enhancement. Thus, in order to produce the desired image enhancement, nitroxide-based agents have to be used at high concentrations that may be unacceptably toxic. Therefore, nitroxides are often combined with other functional molecules in an attempt to extend their effectiveness at concentrations that are tolerable for diagnostic and therapeutic applications.

For example, U.S. Pat. No. 4,863,717 to Keana (1989) describes a long-lasting nitroxide-bearing contrast agent that comprises a large molecule having surfaces covered with nitroxide free radicals and a liposome molecule that encapsulates an oxidant used to reoxidize the reduced nitroxide group back to its paramagnetic form. In U.S. Pat. No. 5,135,737 (1992), Keana also discloses the use of branched organic structures terminating with amine groups to which pharmacologically active groups, such as nitroxides and metal ions, can be chemically attached. These amplifier molecules are utilized to provide a stable contrast agent by combining a plurality of contrast-enhancing groups (such as nitroxides or paramagnetic metal ions) in the various branches of the molecule with a reactive moiety for attaching the molecule to target-specific biomolecules at the site of interest.

In U.S. Pat. Nos. 4,834,964 (1989) and 5,104,641 (1992), Rosen describes MRI image-enhancing agents based on charged, stable, organic nitroxides. Specific classes of nitroxide compounds are disclosed for scanning the spinal cord and organs associated with the cardiovascular system of a patient.

In our copending applications we disclose the use of copolymers containing paramagnetic metal ions dispersed along the copolymer chain, which, because of the size and spatial distribution of the resulting molecule, tends to increase the relaxivity and stability of the contrast agent. In a continuing effort to refine the use of oligomers and polymers as base molecules for introducing paramagnetic material in the human body, the present invention is related to a discovery that enables the design and synthesis of contrast agents with a yet much higher relaxivity than previously reported.

SUMMARY OF THE INVENTION

An object of the present invention is to provide a contrast agent with sufficiently high relaxivity to permit a significant reduction of the dosages of agent used during MRI, thus reducing the patient's exposure to toxic material.

Another object of the invention is to provide a contrast agent that combines cumulatively the image enhancing properties of metal ions and of nitroxides in the same molecule.

A further goal is to provide a general structural framework within which specific contrast agents can be designed for synthetic derivation directed at particular diagnostic or therapeutic objectives.

According to these and other objectives, the present invention consists of novel MRI contrast agents comprising one or more metal-ion chelates in juxtaposition with one or more free-radical nitroxide compounds in a polymeric or oligomeric molecule. Both the chelate units and the free radical units may, independently, be inside the main chain of the polymer or in a side chain of the linkage portion of the polymer. The number of combined units of chelates and free radicals in the polymer or oligomer is at least two.

These and other objects, features and advantages of the present invention, as well as details of the preferred embodiments thereof, will be more fully understood from the following detailed description.

DETAILED DESCRIPTION OF THE PREFERRED EMBODIMENT

The heart of this invention lies in the discovery that metal ion chelates, when juxtaposed to free-radical nitroxides in oligomeric and polymeric molecules, produce a marked increases in relaxivity, greater than either can produce alone. As illustrated by the examples shown in Table 2, relatively low molecular weight oligomeric compounds composed of paramagnetic chelates and nitroxide subunits show a substantial increase in relaxivity when compared to compounds with the same paramagnetic metal ions but without the combination with nitroxides.

TABLE 2

Relaxivity of Hybrid Complexes vs. Similar Non-Hybrid Complexes

| Agent | R1 | R2 |
|---|---|---|
| Mn-EDTA-EOEA-DP | 6.48 ± 0.103 | 13.29 ± 0.40 |
| Mn-Poly(A)-ATMPO | 35.55 ± 1.59 | 57.21 ± 2.09 |
| Mn-Poly-EED-EEA(1) | 38.31 ± 1.03 | 46.31 ± 0.41 |
| Mn-Poly-EED-EEA(2) | 46.55 ± 0.42 | 78.01 ± 1.65 |

(Measurements were taken using 0.5 Tesla and 20 MHz.)

Without limiting the scope of this invention to a specific mechanism of action causing this increase in relaxivity, the inventors hypothesize that the nitroxide radical relaxes other nuclei because of the much larger angular momentum of the unpaired electron spin. In tandem, the paramagnetic center has the same effect, thus producing an additive result. Thus, the resulting extremely high relaxivity of these hybrid contrast agents has applicability for the development of general-purpose vascular imaging and gastrointestinal MRI contrast agents.

In accordance with one preferred generic characterization of the embodiments of this invention, the general structure of a hybrid-polymer contrast agent according to the invention is represented by the following general formula:

$$\left\{ \left[ \begin{array}{c} (Ch)_n - (L)_j \\ | \quad\quad | \\ (M)_k \quad (FR)_m \end{array} \right]_p \left[ \begin{array}{c} (Ch)_n - (FR)_m \\ | \\ (M)_k \end{array} \right]_{p'} \right\}_q \tag{1}$$

wherein Ch is a polynitrilo chelating unit monomer, L is a linker monomer, FR is a nitroxide free radical monomer, and M is a paramagnetic ion;

wherein q=1 to 10,000;

wherein, within each of the q polymeric groups $$\left[ \begin{array}{c} (Ch)_n - (L)_j \\ | \quad\quad | \\ (M)_k \quad (FR)_m \end{array} \right]_p \left[ \begin{array}{c} (Ch)_n - (FR)_m \\ | \\ (M)_k \end{array} \right]_{p'},$$

independently, p=0 to 10,000 and p'=0 to 10,000;

wherein, within each of the p oligomeric groups $$\begin{array}{c} -(Ch)_n - (L)_j - , \\ | \quad\quad | \\ (M)_k \quad (FR)_m \end{array}$$

independently, n=0 to 10,000 and j=0 to 10,000; for each group of paramagnetic ions $$\begin{array}{c} | \\ (M)_k \end{array}$$

chelated by each of the n chelating unit monomers —Ch— in the p oligomeric groups, independently, k=0 to 2; and for each group of free radical monomers $$\begin{array}{c} | \\ (FR)_m \end{array}$$

linked to each of the j linker monomers —L— in the p oligomeric groups, independently, m=0 to 2; and wherein, within each of the p' oligomeric groups $$\begin{array}{c} -(Ch)_n - (FR)_m - , \\ | \\ (M)_k \end{array}$$

independently, n=0 to 10,000 and m=0 to 10,000; and for each group of paramagnetic ions $$\begin{array}{c} | \\ (M)_k \end{array}$$

chelated by each of the n chelating unit monomers —Ch— in the p' oligomeric groups, independently, k=0 to 2.

According to a more special characterization of this invention, a class of hybrid-polymer contrast agents may be represented by the following formula:

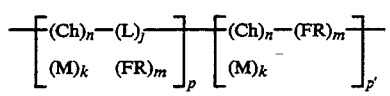 (2)

wherein Ch, L, FR and M are as described above;
wherein, independently, p=1 to 10,000 and p'=1 to 10,000;
wherein, within each of the p oligomeric groups

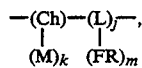

independently, n=0 to 10,000 and j=0 to 10,000; for each group of paramagnetic ions

chelated by each of the n chelating unit monomers —Ch— in each of the p oligomeric groups, independently, k=0 to 2; and for each group of free radical monomers

linked to each of the j linker monomers —L— in each of the oligomeric groups, independently, m=0 to 2; and
wherein, within each of the p' oligomeric groups

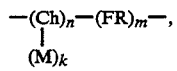

independently, n=0 to 10,000 and m=0 to 10,000; and for each group of paramagnetic ions

chelated by each of the n chelating unit monomers —Ch— in each of the p' oligomeric groups, independently, k=0 to 2.

Note that Formula 2 is a special case of Formula 1 where q=1.

According to another special characterization of the embodiments of the invention, another class of hybrid-polymer contrast agents may be represented by the following formula:

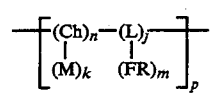 (3)

wherein Ch, L, FR and M are as described above;
wherein p=1 to 10,000; and
wherein, within each of the p oligomeric groups

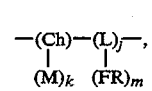

independently, n=0 to 10,000 and j=0 to 10,000; for each group of paramagnetic ions

chelated by each of the n chelating unit monomers —Ch— in each of the p oligomeric groups, independently, k=0 to 2; and for each group of free radical monomers

linked to each of the j linker monomers —L— in each of the oligomeric groups, independently, m=0 to 2.

Note that Formula 3 is a special case of Formula 1 where q=1 and p'=0.

Finally, according to yet another special characterization of the contrast agents of the invention, another class of hybrid polymers may be represented by the following formula:

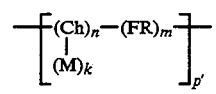 (4)

wherein Ch, FR and M are as described above;
wherein p'=1 to 10,000; and
wherein, within each of the p' oligomeric groups

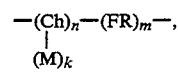

independently, n=0 to 10,000 and m=0 to 10,000; and for each group of paramagnetic ions

chelated by each of the n chelating unit monomers —Ch— in each of the p' oligomeric groups, independently, k=0 to 2.

Note that Formula 4 is a special case of Formula 1 where q=1 and p=0.

The chelating unit monomer Ch in Formulae (1)–(4) is a polynitrilo chelating agent having at least one COOH, COOR$_1$, or COZ group, wherein each R$_1$ is, independently, a C1–C20 substituted or unsubstituted and saturated or unsaturated alkyl or cycloalkyl group or an anhydride, and each Z is, independently, Cl, Br, or I. The COOH groups may, if desired, be in the form of an acid anhydride, as those skilled in the art will recognize, and such variations are intended to be literally encompassed within the term COOH, as employed in connection with the polynitrilo chelating agents of this invention. By substituted, with regard to C1–C20, it is meant substituted with such moieties as OH, NH$_2$, SH, COOH, PO$_4$, and the like. Preferably, R$_1$ is a polyhydroxy-substituted alkyl or cycloalkyl group. By polyhydroxy-substituted alkyl or cycloalkyl group, it is meant that the alkyl or cycloalkyl group is substituted with at least two hydroxyl groups. Suitable substituted and unsubstituted alkyl or cycloalkyl groups, including polyhydroxy-substituted alkyl or cycloalkyl groups, will be readily apparent to those skilled in the art. Preferred polyhydroxy-substituted alkyl or cycloalkyl groups, for example, include sugar alcohols (such as glycidol, inositol, mannitol, sorbitol, pentaerythritol, galacitol, adonitol, xylitol, and alabitol), monosaccharides (such as sucrose, maltose, cellobiose, and lactose), polysaccharides (such as starch), and synthetic polymeric alcohols (such as polyvinylalcohol).

As those skilled in the art understand, a chelating agent is an organic compound capable of combining with a metal (and, particularly for the purposes of this invention, with a paramagnetic ion). Also, by polynitrilo it is meant a compound containing at least two nitrogen groups. Such polynitrilo chelating agents may include either open chain or cyclic structures, as desired. Polynitrilo chelating agents are well known in the art; accordingly, suitable chelating agents for the purposes of this disclosure will be readily apparent to those skilled in the art. Examples of suitable chelating agents include such compounds as ethylenediamine tetraacetic acid (EDTA); diethylenetriamine pentaacetic acid (DTPA); 1,5-di-methoxyethylene-iminocarbonyl-methylene-1,3,5-tricarboxymethylene-1,3,5,-triazapentane; 1,5-di-α,-dihydroxypropeneimino-carbonyl-methylene-1,3,5-tricarboxymethylene-1,3,5-triazapentane; 1,4,7,10-tetraazacyclododecane-1,4,7,10-tetraacetic acid (DOTA); 1,4,7,10-tetraazacyclododecane-N,N',N''-triacetic acid (DO3A); 3,6,9-triaza-12-oxa-3,6,9-tricarboxymethylene-10-carboxy-13-phenyl-tridecanoic acid (B-19036); hydroxybenzyl-ethylenediamine diacetic acid (HBED); N,N'-bis(pyridoxyl-5-phosphate)ethylenediamine-N,N'-diacetic acid (DPDP); 1,4,7-triazacyclononane-N,N',N''-triacetic acid (NOTA); 1-oxa-4,7,10-triazacyclododecane-triacetic acid (OTTA); 1,4,8,11-tetraazacyclotetradecane-N,N',N'',N'''-tetraacetic acid (TETA); triethylenetetraamine hexaacetic acid (TTHA); 1,2-diaminocyclohexane-N,N,N',N'-tetraacetic acid; as well as anhydrides of the foregoing compounds, such as, for example, ethylenediamine dianhydride (EDTA-dianhydride) and diehtylenetriamine pentaacetic acid dianhydride (DTPA-dianhydride). Preferably, the complexing agents are DTPA, EDTA and DOTA, most preferably DTPA and EDTA. Examples of these and other chelating agents are described in U.S. Pat. No. 4,933,441 to Gibby, the disclosure of which is hereby incorporated by reference in its entirety.

Many of the foregoing chelating agents are available commercially, such as, for example, ethylenediamine tetraacetic acid (and its anhydride) and diethylenetriamine pentaacetic acid (and its anyhydride), which may be purchased from the Aldrich Chemical Co. of Milwaukee, Wis., or from the Sigma Chemical Co. of St. Louis, Mo. Such chelating agents may also be prepared by conventional techniques, as would be readily apparent to those skilled in the art.

The free radical monomer Fr in Formulae (1)–(4) above consists of heterocyclic or non-heterocyclic nitroxide monomers. The heterocyclic nitroxides have the following general structure:

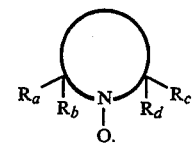

wherein a five member ring is pyrrolidine, oxazolidine, imidazolidine, or thiazolidine; a six member ring is piperidine; and each of the four substitute radicals Ra, Rb, Rc, Rd is, independently, a C1-C20 (substituted or unsubstituted and saturated or unsaturated) alkyl or cycloalkyl group, interrupted or terminated with OH, SH, NH$_2$, NHR$_1$, COOH, COOR$_1$, NCS, COCHCH$_2$, or COZ, where Z and R$_1$ are as described above. Non-heterocyclic nitroxides comprise diphenylnitroxide and di-tert-butyl nitroxide.

Preferred for this invention are the following nitroxide stable free radicals: 2,2,6,6-tetramethylpiperidine-1-oxyl; 2,2,4,4-tetramethyl-pyrrolidine-1-oxyl; 2,2,4,4-tetramethylimidazolidine-3-oxyl; 2,2,4,4-tetramethyl-1,3-thiazolidine-3-oxyl; 2,2,4,4-tetramethyl-1,3-oxazolidine-3-oxyl; 2,2,6,6-tetramethylpyrimidine-1-oxyl; diphenylnitroxide; and di-tertbutylnitroxide; wherein each nitroxide may have one or more OH, SH, NH$_2$, NHR$_1$, COOH, COOR$_1$, NCS, COCHCH$_2$, or COZ, Z and R$_1$ being as described above.

These nitroxide monomers may be combined with one or two functional groups. Monofunctionalized nitroxide monomers comprise 1-oxyl-2,2,6,6-tetramethyl-4-piperidinyl acrylate; 4-(iodomethylenecarbonylimino)-2,2,6,6-tetramethyl-piperdinyl-1-oxy; 4-(bromomethylenecarbonylimino)-2,2,6,6-tetramethyl-piperidinyl-1-oxy; 3-carboxy-2,2,5,5-tetramethylpyrrolidinyl-1-oxy; 3-chlorocarbonyl-2,2,5,5-tetramethyl-pyrrolidinyl-1-oxy; 3-aminomethylene-2,2,5,5-tetramethylpyrrolidinyl-1-oxy; 3-hydroxymethylene-2,2,5,5-tetramethylpyrrolidinyl-1-oxy; 3-hydroxy-2,2,5,5-tetramethylpyrrolidine-1-oxyl; 3-chloroformyl-2,2,5,5-tetramethylpyrrolidine-1-oxyl; 4-amino-2,2,6,6-tetramethylpiperidine-1-oxyl; 4-hydroxy-2,2,6,6-tetramethylpiperidine-1-oxy; and 3-thiocabamoylmethylene-2,2,5,5-tetramethylpyrrolidinyl-1-oxy.

Difunctionalized nitroxide monomers comprise cis-1-oxyl-2,2,5,5-tetramethylpyrrolidine; trans-1-oxyl-2,2,5,5-tetramethylpyrrolidine; 3-amino-4-aminomethylene-2,2,5,5-tetramethylpyrrolidine; cis-2,5-dimethyl-2(aminomethyl)-5-(2-carboxyethyl)-tetrahydropyrrole-1-oxyl; cis-2,5-dimethyl-2-(hydroxymethyl)-5-(methoxycarbonylmethyl)-tetrahydropyrrole-1-oxyl; cis-2,5-dimethyl-2-(hydroxymethyl)-5-(2-hydroxyhexyl)tetrahydropyrrole-1-oxyl; cis-2,5-dimethyl-2,5-bis(3-hydroxypropyl)-pyrrolidinyl-1-oxy; trans-2,5-dimethyl-2,5-bis(3-hydroxypropyl)-pyrrolidinyl-1-oxy; trans-2,5-dimethyl-2,5-bis(2-carboxyethyl)-pyrrolidinyl-1-oxy; cis-2,5-dimethyl-2,5-bis(2-hydroxy-5-methylphenyl)-tetrahydroxypyrrol-1-oxy; 3-amino-4-carboxy-2,2,5,5-tetramethylpyrrolidinyl-1-oxy; 2,5-di-tert-butyl-3,4-diethyloxycarbonyl-pyrrol-1-oxyl; and 1,4-bis(4-hydroxy-2,2,6,6-tetramethyl-1-oxyl-4-piperidyl)-butane.

In Formulae (1), (2) and (3), L is linker monomer having the following general structure:

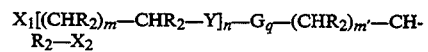

wherein $X_1$ and $X_2$ are, independently, OH, $NH_2$, $NHR_1$, COOH, $COOR_1$, SH, Z or NCS; Y is O, NH, $NR_1$, S or CO; each Z and each $R_1$ are, independently, as described above; $R_2$ is a C1–C20 substituted or unsubstituted, saturated or unsaturated, alkyl or cycloalkyl group; G is a C1–C20 substituted or unsubstituted alkyl or cycloalkyl group, a saccharide, a peptide or a polysulfide; and m, m', n, and q are, independently, 0 to 10,000. With regard to the C1–C20 groups, by substituted it is meant the same substituting moieties as described above for $R_1$ in the formulation of polynitrilo chelating agents.

Suitable polyamino linker monomers comprise compounds such as 1,2-diaminoethane; 1,3-diaminopropane; 1,4-diaminobutane; 1,5-diamino-3-(2-aminoethyl)-pentane; N,N'-dimethyl-1,2-diaminoethane; N,N'-dimethyl-1,3-diaminopropane; 2-hydroxy-1,3-diaminopropane; 2-amino-1,3-diaminopropane; 2,3-diamino-1,4-butanediol; 1,4-diamino-2,3-butane diol; 1,4-diaminocyclohexane; 1,4-phenylenediamine; 1,1,1-tris-(aminomethyl)ethane; 2,2',2''-tris-aminoethylamine; tris-(aminomethylene)methane; diethylenetriamine; triethylenetetraamine; 1,3,5-triaminocyclohexane; and 1,3,5-triaminobenzene.

Suitable polyhydroxy linker monomers comprise compounds such as 2,2-dimethyl-1,3-propanediol; tris-(2-hydroxyethyl)amine; 1,1,1-tris-(hyroxymethylene)ethane; glycerine; erythritol; sugar alcohols; polyethyleneglycol; w,w'-diamino-polyethyleneglycol; N-substituted-w-aminopolyethyleneglycol; w,w'-dithiol-polyethyleneglycol; polysulfide-blocked polyethyleneglycol; and polyethylene-imine.

Most preferred linker monomers are ethylenedioxydiethylamine; N,N'-bis-dihydroxypropyl-ethylenedioxydiethylamine; and ethylenedioxydiethylmercaptane.

The molecular weight of a copolymer having a structure according to one of the disclosed formulae can vary as widely as desired. Preferably, however, the molecular weight of such copolymer is between 1,000 and 500,000 (weight-average molecular weight), and most preferably between 3,000 to 30,000.

The copolymer may be prepared by using polycondensation polymerization techniques. Such polymerization techniques include those described in McCrum et al., *Principles of Polymer Engineering*, Oxford University Press (New York 1988), which is hereby incorporated herein by reference in its entirety. The monomers bind to one another to form a copolymer through an ester, amide, or carboxylic thioester linkage of at least one of the reactive functional groups OH, $NH_2$, $NHR_1$, COOH, COZ, $COOR_1$, SH, NCS, $COCHCH_2$, or Z groups in each monomer. If desired, one may employ any one of a number of condensation reagents such as dicyclohexylcarbodiimide (DCC), to facilitate the polymerization reaction. Also, if desired, polynitrilo chelating agents may be employed in the form of acid anhydrides to facilitate the polymerization reaction.

As those skilled in the art will recognize, the copolymer may take any one of a variety of forms such as linear, branched, cyclic and/or cross linked, depending upon the particular monomers employed, the number of reactive sites that the monomers possess, the particular reaction conditions, etc., as would be apparent to those skilled in the art. The copolymer may consist of more than one type of chelating unit monomer, more than one type of nitroxide free radical monomer, and more than one type of linker monomer.

In accordance with the main aspect of the invention, the copolymer further comprises paramagnetic ions chelated into the polynitrilo chelating unit Ch, which renders the invention particularly suited for magnetic resonance imaging. Exemplary paramagnetic ions suitable for use in the present invention comprise the transition elements and lanthanides. Preferred elements include Gd(III), Mn(II), Cu(II), Cr(III), Fe(II), Fe(III), Co(II), Er(II), Ni(II), Eu(III), Dy(III), Yb(III), and Ho(III). The most preferred elements are Gd(III), Mn(II) and Fe(III). If desired, different paramagnetic ions may be employed in combination with one another and may be chelated to a combination of different chelating units within the polymer chain.

The following examples are provided to illustrate the invention.

Example 1

Synthesis of Manganese Poly-EDTA-(2,2'-ethylenedioxydiethylamine)-(2,2,6,6-tetramethyl-1-oxyl-piperidin-4-yl acrylate) [Mn-Poly(A)-ATMPO]

Poly-EDTA-2,2'-(ethylenedioxy)-diethylamine (EOEA) was first synthesized by dissolving 3.16 g (0.021M) of 2,2'-(ethylenedioxy)-diethylamine in 75 ml of dry methanol; by suspending 4.60 g (0.018M) of ethylenediamine tetracetic dianhydride in 75 ml of dry methanol; and by adding the suspension dropwise to the first solution over the course of about 1.5 hours while continuously stirring. Stirring was further continued for another 5 hours at room temperature.

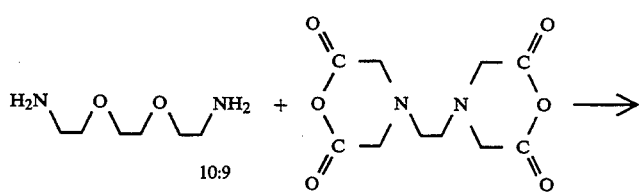

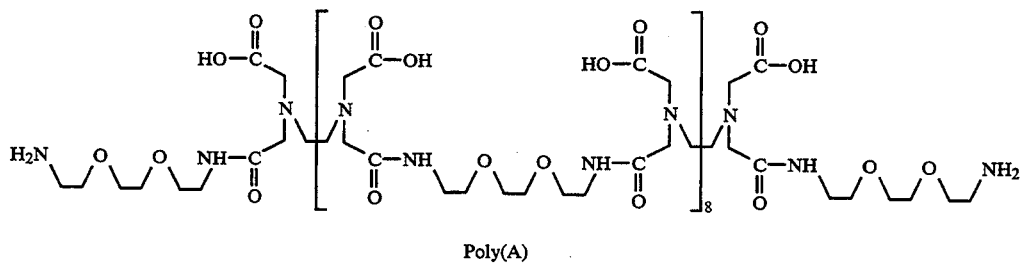

Poly(A)

At the end of this time, it was no longer possible to see the suspended EDTA-dianhydride. The admixture was kept overnight. The solution was then heated and kept at about 40°–45° C. for 8 hours in order to ensure the completion of the polymerization reaction. The unreacted dianhydride was filtered out and the solvent was evaporated off the solution, yielding 7.49 g (96.5% yield) of Poly(A), a white foamy solid.

2,2,6,6-tetramethyl-1-oxyl-piperidin-4-yl acrylate (ATMPO) was then synthesized by dissolving 10 g of 4-OH-2,2,6,6-TMP-1-oxyl and 10.53 g of triethylamine (TEA) in 100 ml of $CH_2Cl_2$ and cooling the solution to about 0° to 4° C.; further by dissolving 4.74 g of acryloyl chloride in 20 ml of $CH_2Cl_2$ and adding this solution dropwise into the first solution while stirring at about 0°–4° C.

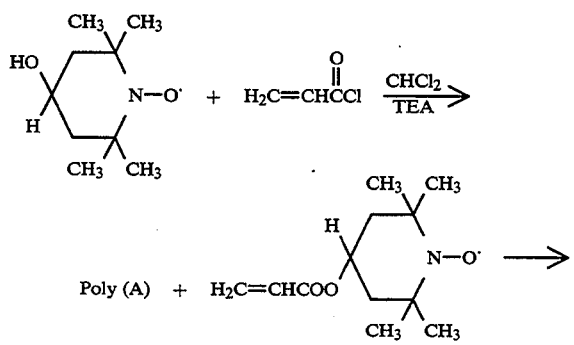

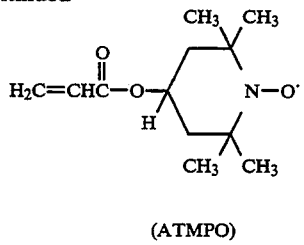

(ATMPO)

Stirring continued for another hour, when a precipitate was observed in the reaction solution. The temperature of the solution was then raised to room temperature and left overnight. The precipitate was filtered and washed with water. The organic layer was separated and dried over anhydrous sodium sulfate. The $CH_2Cl_2$ was evaporated leaving a red solid (ATMPO) which was recrystallized with hexane. The melting point was determined to be 99° C.

Poly(A) and ATMPO were then combined to synthesize Poly(A)-ATMPO as follows:

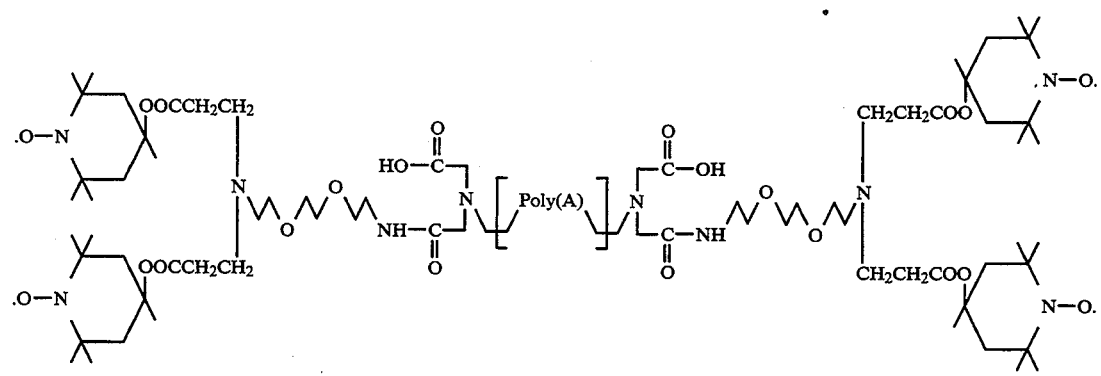

1.43 g of Poly(A) was dissolved in 40 ml of water and 50 ml of $CH_3CN$. 0.37 g of ATMPO was dissolved in 25 ml of $CH_3CN$. These solutions were then mixed, heated and kept at about 80° C. for 3 hours and left at room temperature overnight. This mixture was then refluxed at about 90°–95° C. for 5 hours. The solvents were evaporated off and 1.8 g of red orange solid Poly(A)-ATMPO resulted, with a 100% yield.

Finally, the polymer was chelated to yield the Mn-Poly(A)-ATMPO as follows:

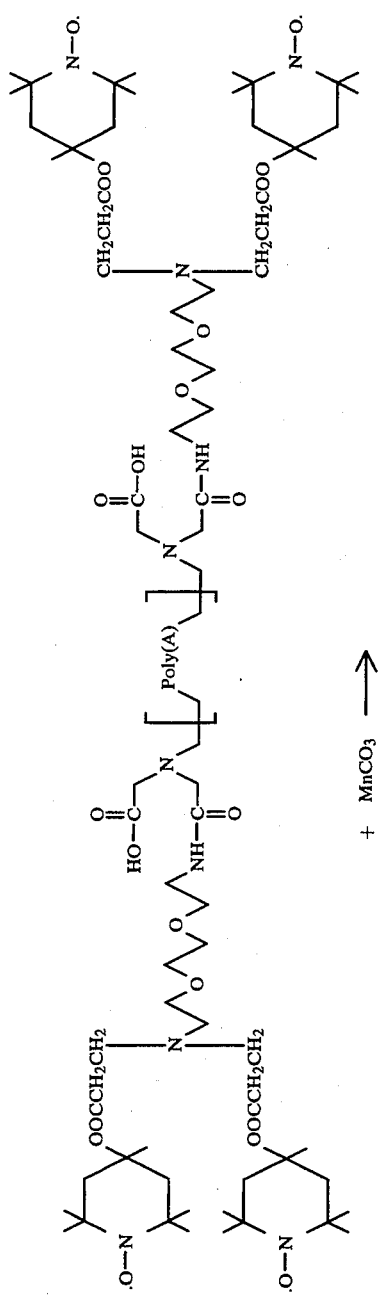
+ MnCO₃ →
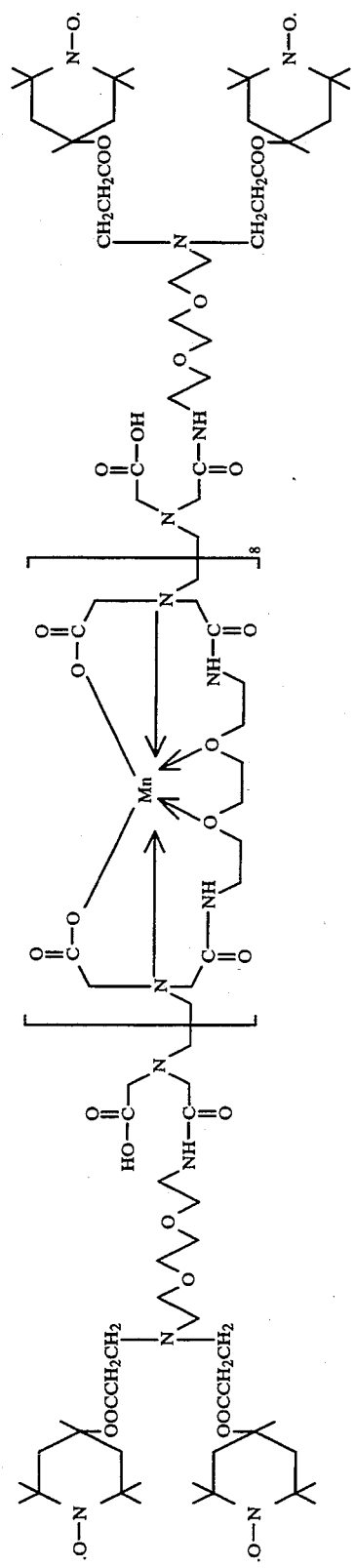

1.67 g of Poly(A)-ATMPO, 0.60 g of MnCO$_3$ and 100 ml of water were heated and maintained at about 40° C. for 5 hours. The temperature was then raised to about 70° C. and kept there for 2 hours. Unreacted MnCO$_3$ was filtered out and the water evaporated. 1.43 g of orange solid resulted [yield of 76% Mn-Poly(A)-ATMPO].

Example 2

Synthesis of Mn-Poly-EED-EEA (First Method)

EOEA (2,2'-ethylenedioxydiethylamine) was first reacted with 2,2,6,6-tetramethyl-1-oxyl-piperidinyl-4-yl acrylate (ATMPO) to produce EOEA-ATMPO (Component 1), as follows:

N,N'-(2,3-dihydroxypropyl)-2,2'-(ethylenedioxy)-diethylamine (EOEA-DP) was then synthesized as follows:

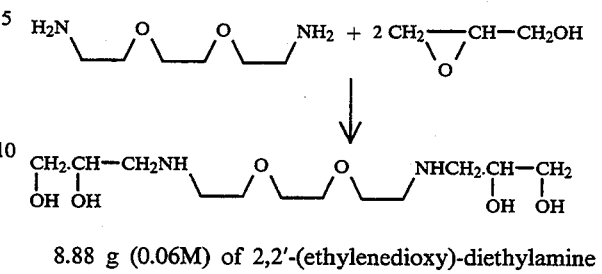

8.88 g (0.06M) of 2,2'-(ethylenedioxy)-diethylamine

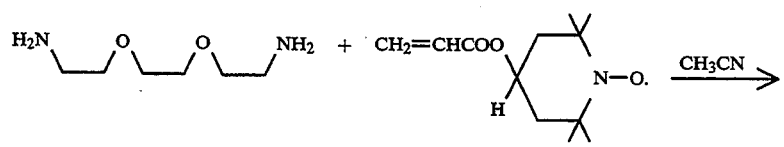

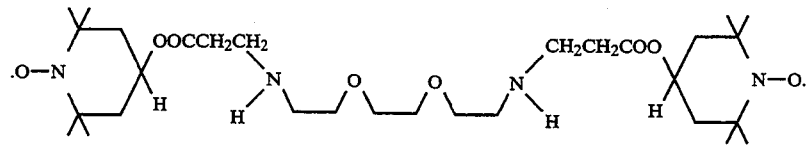

0.56 g (0.0025M) of ATMPO (prepared as illustrated in Example 1) and 0.25 g (0.0017M) of EOEA were dissoved in 50 ml CH$_3$CN and stirred at room temperature for about 3 hours and refluxed for about 8 hours. The CH$_3$CN was evaporated and a viscous EOEA-ATMPO liquid resulted (100% yield).

(EOEA) was dissolved in 50 ml of dry methanol and heated to about 60° C. 8.88 g of glycidol (0.12M) was added dropwise under stirring over the course of approximately 2 hours in a water bath at about 70° C. Stirring was continued for about an additional hour at which time the methanol was evaporated off. A viscous liquid EOEA-DP (Component 2) resulted (100% yield).

Poly-EED-EEA was then synthesized as follows:

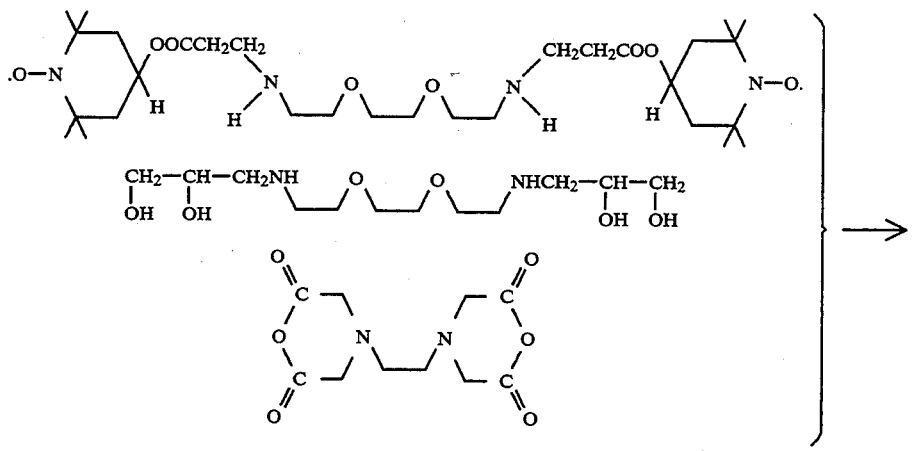

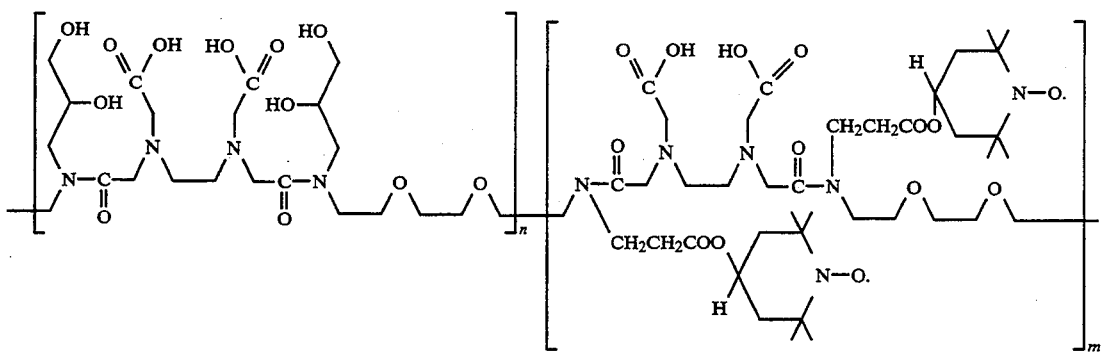

0.81 g (0.00135M) of EOEA-ATMPO (Component 1) was dissolved in 10 ml of dry methanol. 1.91 g (0.0065M) of EOEA-DP (Component 2) was dissolved in 20 ml of dry methanol. These two solutions were mixed together. 1.9968 g (0.0078M) of EDTA-dianhydride (Component 3) was suspended in 20 ml dry methanol. This suspension was added to the solution containing Components 1 and 2 and stirred at about 50° C. for approximately 2 hours. The methanol was evaporated off and 4.99 g of Poly-EED-EEA were obtained (approximately 100% yield).

Finally, the Poly-EED-EEA was chelated as follows:

MnCO₃ +

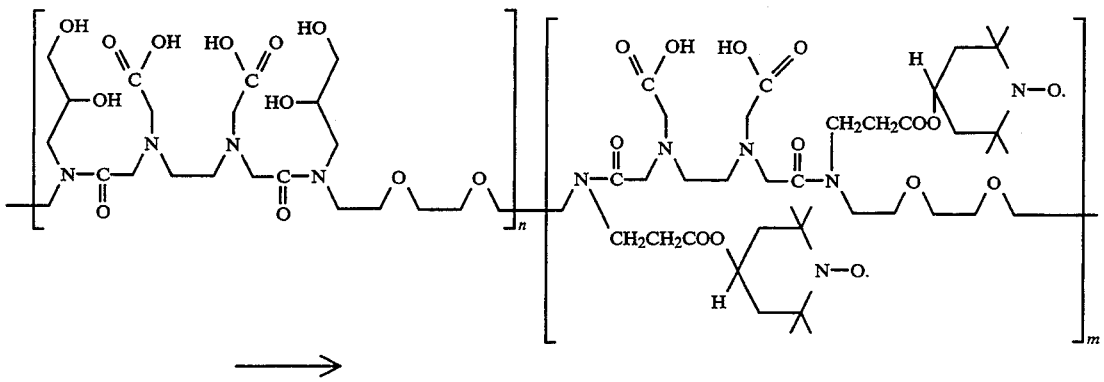

⟶

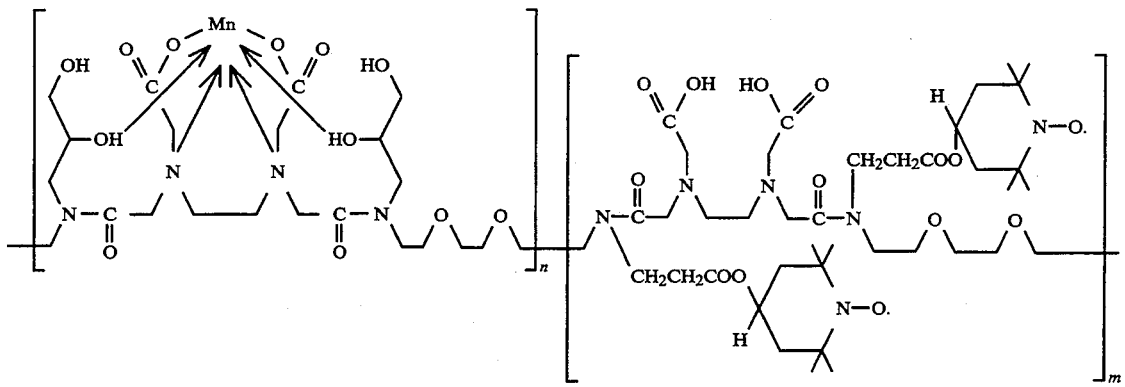

4.94 g (0.00141M) of Poly-EED-EEA was reacted with 0.17 g (0.00147M) of MnCO₃ in water at about 40° C. for about 2 hours; then the temperature was raised to about 70° C. for approximately 2 additional hours. The product was then filtered and the unreacted nitroxide was extracted with 30 ml of ethylacetate. The organic layer was separated off. The water was evaporated and the residue dried in a vacuum oven. This yielded 4.49 g (89.8% yield) of orange solid Mn-Poly-EED-EEA. The molecular weight of the polymer was 3559. The percentage of manganese was found to be 1.46% by structure and 1.45% by analysis.

Example 3

Synthesis of Mn-Poly-EED-EEA (Second Method)

EOEA was first reacted with 2,2,6,6-tetramethyl-1-oxyl-piperidinyl-4-yl acrylate (ATMPO) to produce EOEA-ATMPO (Component 1), as shown in Example 1 above.

Similarly, N,N'-(2,3-dihydroxypropyl)-2,2'-(ethylenedioxy)diethylamine (EOEA-DP) was synthesized to produce Component 2 as shown in Example 2.

Poly-EED-EEA was also synthesized as shown in Example 2 by combining EOEA-ATMPO (Component 1) with EOEA-DP (Component 2) and then by mixing the resulting solution with EDTA-dianhydride (Component 3).

Finally, the Poly-EED-EEA was chelated according to the following second method:

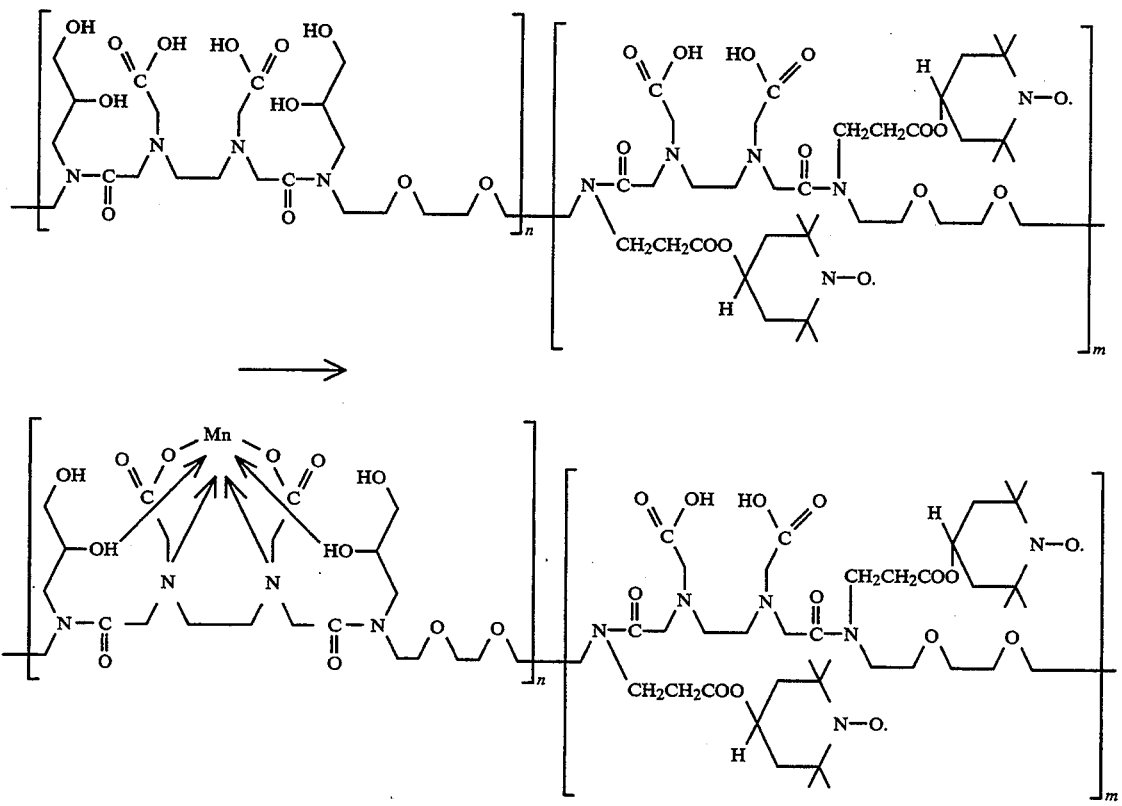

1.24 g (0.3537 mM) of Poly-EED-EEA was reacted with 0.194 g (1.6876 mM) of $MnCO_3$ in water at about 40° C. for about 8 hours; then the temperature was raised to about 70° C. for approximately 1 additional hour. The water was then evaporated off and a 100% yield of solid Mn-Poly-EED-EEA was provided. The molecular weight of the polymer was 3760. The percentage of manganese was found to be 7.01% by structure and 6.6% by analysis.

Example 4

Synthesis of Gd-Poly-DTPA-DiaminoPROXYL

Poly-DTPA-diaminoPROXYL is first synthesized according to the following reaction shown by H. R. Wenzel et al. in Chemische Berichte 111, 2453 (1978):

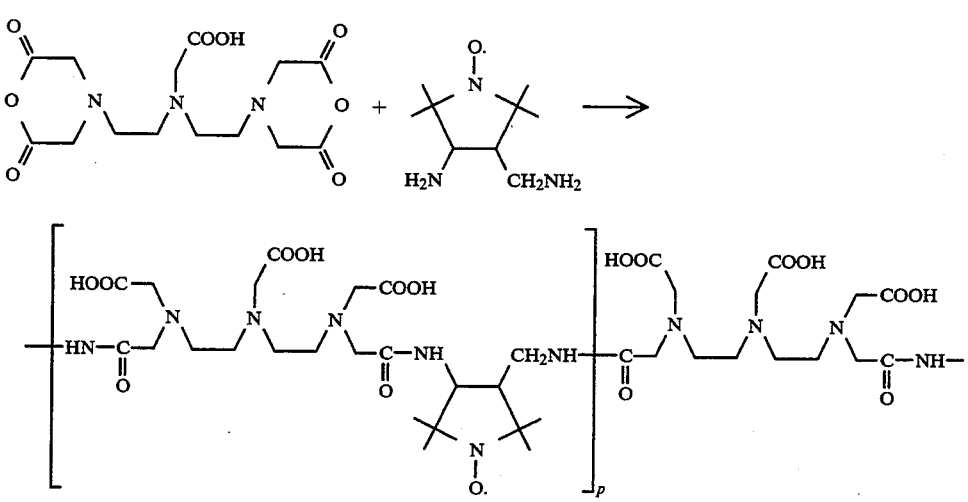

3.57 g of DTPA-dianhydride and 1.86 g of 2,2,5,5-tetramethyl-3-amino-4-aminomethylene-pyrrolidine-1-oxyl are mixed in anhydrous methanol, stirred at room temperature overnight, and evaporated to dryness. This process produced 5 g of poly-DTPA-PROXYL copolymer.

The chelate was then prepared by dissolving 5.43 g poly-DTPA-PROXYL in 100 ml of water, suspending 2 g of gadolinium oxide in the solution, stirring at about 45° C. for approximately 10 hours, and filtering the excess gadolinium oxide out. The solution was then evaporated until dry. 6.5 g of Gd-poly-DTPA-PROXYL was thus obtained having the following structure:

Example 5

Synthesis of Gadolinium-DOTA-Poly-ethylenedioxydiethylamine-PROXYL

Poly-ethylenedioxydiethylamine-PROXYL (poly-DOEA-PROXYL) is first synthesized as follows, as shown by Keanna, J. F. W. et al, Can. J. Chem., 60, 1439 (1982):

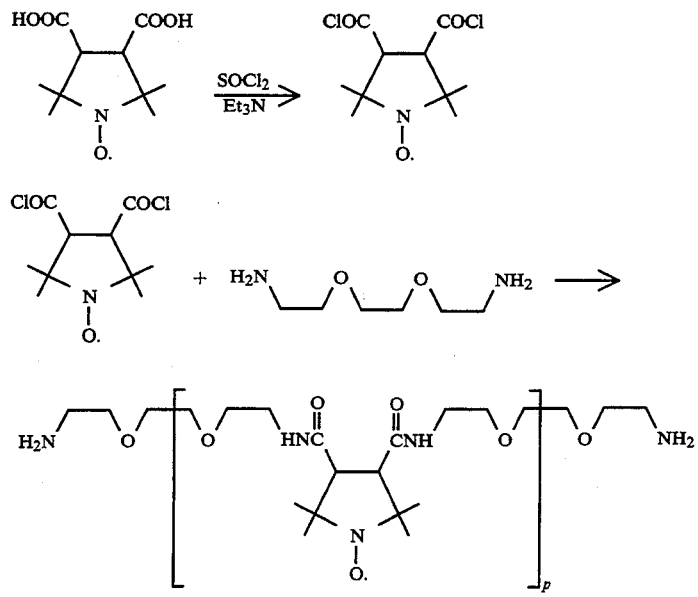

6.13 g of cis-1-oxyl-2,2,5,5-tetramethyl-3,4-dicarboxypyrrolidine and 5.3 g of dried triethylamine were dissolved in 50 ml of chloroform. 6.3 g of freshly distilled sulfonyl chloride was added at about 0° to 5° C., drop by drop, while stirring, and then stirred for approximately 2 additional hours. The reaction mixture was

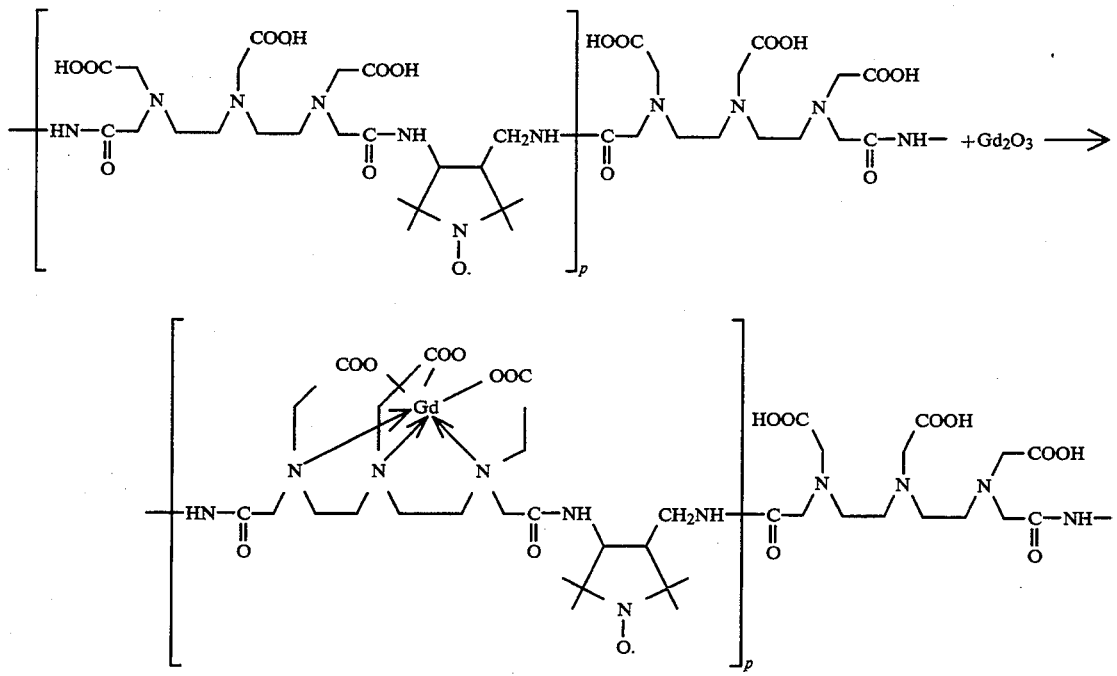

evaporated to remove the chloroform and traces of unreacted sulfonyl chloride and triethylamine. The residue was redissolved into 50 ml of chloroform, yielding a 3,4-dichlorocarbonyl-2,2,5,5-tetramethylpyrrolidine-1-oxyl (di-Cl-PROXYL) product.

The solution of di-Cl-PROXYL thus obtained was added to 4.44 g of ethylenedioxydiethylamine dissolved 100 ml of chloroform, drop by drop at about 0° to 5° C.; the resulting mixture was stirred for about 5 hours, and then evaporated to dryness. The process yielded the amino-terminated copolymer shown above, having a molecular weight of about 3,000.

The copolymer was then combined with 1,4,7,10-tetraazacyclododecane-1,4,7,10-tetraacetic acid (DOTA) according to the following reaction:

above in 50 ml of chloroform was added to the mixture, at about 0° to 5° C., and then stirred for approximately 6 hours. The reaction mixture was evaporated to dryness and then redissolved in 30 ml of water. The precipitate dicyclohexylurea was filtered out, and the solution was reacted with acetone to produce a viscous solid precipitate consisting of DOTA-poly-EOEA-PROXYL. The product was washed several times with acetone and dried under vacuum.

Finally, Gd-DOTA-poly-ethylenedioxydiethylamine-PROXYL (Gd-DOTA-poly-EOEA-PROXYL) was obtained by chelating the polymer with gadolinium oxide. 4 g of DOTA-poly-EOEA-PROXYL were dissolved in 100 ml of water, and 0.5 g of a gadolinium oxide suspension were stirred into this solution at about

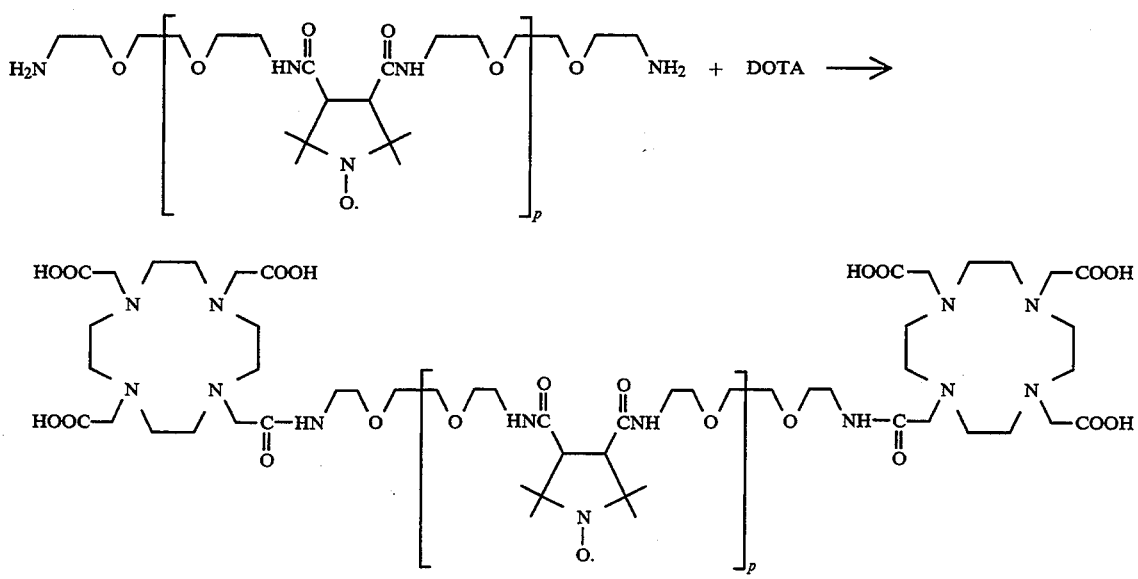

0.81 g of 1,4,7,10-tetraazacyclododecane-1,4,7,10-tetraacetic acid was dissolved in 30 ml of chloroform; a solution of 0.51 g of dicyclohexylcarbodiimide (DCC) in 20 ml of chloroform was then added and stirred for about 4 hours. A solution of 3.2 g of the amino-terminated copolymer prepared according to the step 40° C. for approximately 24 hours. The excess gadolinium oxide was filtered out and the solution was evaporated dry, thus producing a chelated Gd-DOTA-poly-EOEA-PROXYL copolymer of the following structure:

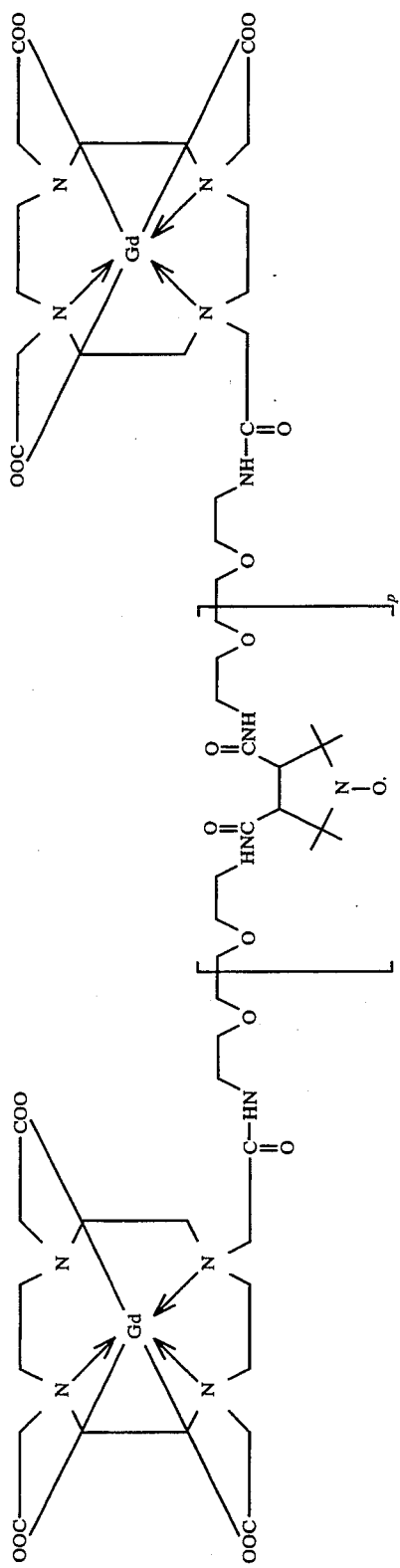

As demonstrated by these examples and as one skilled in the art would recognize, the invention has a wide range of applications for creating contrast agents with great improvements in relaxivity. The exact formulation of a specific contrast agent will vary depending upon the intended use and will include small molecular-weight chelates such as a single monomeric chelate unit with one or more R groups bearing one or more nitroxide units, an oligomer with several chelates and several nitroxide units, a polymer comprising many chelate and nitroxide units, branching or star shaped compounds with many chelates and nitroxide units (e.g. branching polymers), and particles, either gel-like or solid, containing many nitroxides and metal ions or metal oxides. The key is that the metal ions and nitroxides are in juxtaposition or close approximation to one another to achieve the increase in relaxivity of this invention.

As indicated above, the extremely high relaxivity of these contrast agents has applicability particularly for the development of general purpose vascular imaging and gastrointestinal MRI contrast agents. Low molecular weight contrast agents, e.g. under 10,000 molecular weight, are preferred as general purpose agents for the central nervous system, particularly as markers of cerebral perfusion and blood brain barrier breakdown. Additionally, these smaller compounds may be used as targeted agents attached to peptides, antibodies, glycoproteins, liposomes and carbohydrate moieties. Higher molecular weight compounds, e.g. over 10,000 MW, may be designed as blood pool contrast agents and likewise used for in vivo targeting. Compounds over 30,000 MW generally have a longer intravascular half-life and compounds over 60,000 MW will generally not be excreted by the kidneys until broken down into smaller subunits.

These hybrid contrast agents may also be formulated as nanoparticles wherein one or more paramagnetic ions is held together with one or more nitroxides, so as to create particles with extremely high relaxivity and longer intravascular half-life. These particles may be designed to be either paramagnetic or superparamagnetic.

Polymers useful in the present invention can be of natural or synthetic or semisynthetic origin. The term semisynthetic polymer, as employed herein, denotes a natural polymer that has been chemically modified in some fashion. Preferably, the polymer is natural or semisynthetic, most preferably natural. Further, as used herein, the term polymer denotes a compound comprised of two or more repeating monomeric units, preferably three or more repeating monomeric units, more preferably five or more repeating units, and most preferably ten or more repeating units.

Exemplary natural polymers suitable for use in the present invention may include naturally occurring polysaccharides such as, for example, arabinans, fructans, fucans, galactans, galacturonans, glucans, mannans, xylans (e.g., inulin), levan, fuciodan, carrageenan, galactocarolose, pectins (including high methoxy pectin and low methoxy pectin; low methoxy pectin denoting pectin in which less than 40% of the carboxylic acid groups are esterified and or amidated, and high methoxy pectin denoting pectin in which 40% or more of the carboxylic acid groups are esterified and/or amidated), pectic acids, amylose, pullulan, glycogen, amylopectin, cellulose, dextran, pustulan, chitin, agarose, keratin, chondroitin, dermatan, hyaluronic acid, alginic acid, xanthan gum, starch, and various other natural homopolymers or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid; as well as naturally occurring derivatives thereof such as polygalacturonic acid (and other polyuronic acids, such as polyglucuronic acid, polymannuronic acid, polyguluronic acid, hyaluronic acid, etc.) and cellulose. Exemplary natural polymers may also include, for example, polypeptides and polyalcohols, as will be readily apparent to those skilled in the art.

Exemplary semisynthetic polymers include such modified natural polymers as carboxymethylcellulose, hydroxymethylcellulose, hydroxypropylmethylcellulose, methylcellulose and methoxycellulose.

Exemplary synthetic polymers suitable for use in the present invention include polyethylenes (such as, for example, polyethylene glycol, polyoxyethylene, polyoxyethylene glycol, and polyethylene terephthlate), polypropylenes (such as, for example, polypropylene glycol), polyurethanes (such as, for example, polyurethane ureas), pluronic acids and alcohols, polyvinyls (such as, for example polyvinyl alcohol, polyvinylchloride and polyvinylpirrolidone), nylon, polystyrene, polyactic acids, fluorinated hydrocarbons, fluorinated carbons (such as, for example, polytetrafluoroethylene), polyacrylates (such as, for example, polymethylmethacrylate), polyacrylic acids (such as, for example, polymethacrylic acid) and polyacrylamides, as well as derivatives thereof.

Preferred polymers include polygalacturonic acid and pectins. As those skilled in the art are aware, pectins are generally methyl esters of polygalacturonic acid. The polymers may be cross-linked, if desired. Preferably, however, the polymers are not cross-linked. It is also recognized that some polymers may be prepared by chemically modifying naturally occurring polymers. Such chemically modified natural polymers are to be considered within the scope of the phrase natural polymer, as used herein.

The polymers of the present invention may be employed in various shapes and forms, such as fibers, beads, and particles. The polymers may also be of varying molecular weight, including high molecular weight polymers (that is, equal to or greater than 30,000 weight-average molecular weight). For reasons of diagnostic efficacy, preferably the polymers are low molecular weight polymers, more preferably having a molecular weight (weight average) of about 25,000 or less, still more preferably less than about 20,000, even more preferably less than about 15,000, and most preferably less than about 10,000. One highly preferable weight average molecular weight range is between about 1,500 and about 25,000.

Polyethylene glycol (PEG), a synthetic polymer that exhibits a high water binding capacity, is particularly preferred for use in the subject invention. Due to their high water binding capacity and the accompanying decrease in the amount of free water in solution, PEG and similar polymers serve to alter the proton density in solution. Furthermore, PEG is used for the fractional precipitation of proteins from solution, which is believed to be due in part to the excluded volume effects caused by this polymer, whereby the protein is excluded from regions of the solution occupied by the polymer and is concentrated in the water spaces, that is, the extrapolymer spaces between the individual molecules of the polymer. For these and other reasons, PEG and related polymers are particularly preferred polymers for the subject invention. PEG, as well as other synthetic polymers, may be prepared, in varying molecular weights, using conventional methodology.

If desired, the contrast medium may further comprise a physiologically compatible suspending or viscosity-increasing agent, referred to herein collectively as a suspending agent. The phrase suspending agent is intended to denote a compound that assists in providing relative uniformity or homogeneity to the contrast medium. A number of such agents are available, including xanthan gum, acacia, agar, alginic acid, aluminum monostearate, bassorin, karaya, gum arabic, unpurified bentonite, purified bentonite, bentonite magma, carbomer 934P, calcium carboxymethylcellulose, sodium carboxymethylcellulose, carboyymethylcellulose sodium 12, carrageenan, cellulose (microcrystalline), dextran, gelatin, guar gum, hydroxyethylcellulose, hydroxypropylcellulose, hydroxypropylmethylcellulose, magnesium aluminum silicate, methylcellulose, pectin, casein, polyethylene oxide, polyvinyl alcohol, povidone, propylene glycol, alginate, silicon dioxide, silicon dioxide colloidal, sodium alginate and other alginates, and tragacanth. As those skilled in the art would recognize, wide ranges of suspending agents can be employed in the contrast medium of the invention, as needed or desired. Preferably, however, the suspending agent is present in an amount of at least about 0.05% by weight, more preferably at least about 0.1% by weight, and generally less than about 1% by weight, more preferably less than about 0.5% by weight.

In addition, in order to cause gelation with polymers and metals that do not gel spontaneously, or to enhance gelation, gelling agents such as polyvalent metal cations, sugars and polyalcohols may be employed. Exemplary polyvalent metal cations useful as gelling agents include calcium, zinc, manganese, iron and magnesium. Useful sugars include monosaccharides such as glucose, galactose, fructose, arabinose, allose and altrose; disaccharides such as maltose, sucrose, cellobiose and lactose; and polysaccharides such as starch. Preferably, the sugar is a single sugar, that is, a monosaccharide or a disaccharide.

Polyalcohol gelling agents useful in the present invention include, for example, glycidol, inositol, mannitol, sorbitol, pentaerythritol, galacitol and polyvinylalcohol. Most preferably, the gelling agent employed in the present invention is sucrose and/or calcium. The particular gelling agents which may be employed in the various formulations of the present invention will be readily apparent to one skilled in the art in view of the present disclosure.

Since the compositions of the invention are used as intravascular agents, osmolarity is important to prevent blood cell damage. It should be approximately the same value as that of human blood. As those skilled in the art will recognize, the osmolarity of a solution may be controlled by regulating the use of osmotically active materials in the contrast medium formulation. Osmotically active materials include such physiologically compatible compounds as monosaccharide sugars or sugar alcohols, disaccharide sugars, amino acids and various synthetic compounds. Suitable monosaccharide sugars or sugar alcohols include, for example, erythrose, threose, ribose, arabinose, xylose, lyxose, allose, altrose, glucose, mannose, idose, galactose, talose, ribulose, fructose, sorbitol, mannitol and sedoheptulose, with preferable monosaccharides being fructose, mannose, xylose, arabinose, mannitol and sorbitol. Suitable disaccharide sugars include, for example, lactose, sucrose, maltose, and cellobiose. Suitable amino acids include, for example, glycine, serine, threonine, cysteine, tyrosine, asparagine, glutamine, aspartic acid, glutamic acid, lysine, arginine and histidine. Synthetic compounds include, for example, propylene glycol, polypropylene glycol, ethylene glycol, polyethylene glycol and polyvinylpyrrolidone. Various other suitable osmotically active materials are well known to those skilled in the art, and are intended to be within the scope of the term osmotically active agent, as used herein.

Typically, to achieve the preferred ranges of osmolarity in the contrast medium of the invention, less than about 25 g/l, more preferably less than about 20 g/l, even more preferably less than about 15 g/l, and most preferably less than about 10 g/l of the osmotically active materials are employed, and in some instances no osmotically active material is used. A most preferred range of osmotically active material is between about 1 and 10 g/l.

Although the most desirable pH for the contrast medium of the present invention may vary, as those skilled in the art will recognize, the preferred pH range for most diagnostic uses is generally between about 3 and about 10 pH units, more preferably between about 5 and 8 pH units. The desired pH can be achieved and maintained through the use of physiologically compatible pH regulating additives such as suitable bases, buffers and the like, as one skilled in the art will recognize. Particularly preferred buffers include sodium acetate and glacial acetic acid buffer.

Many of the compounds used for the synthesis of the contrast agents of this invention are available commercially. The compounds may also be prepared by conventional techniques such as the polymerization techniques described in McCrum et al., referenced above.

Thus, while the invention has been particularly shown and described with reference to preferred embodiments thereof, it will be understood by those skilled in the art that changes in form and detail may be made therein without departing from the spirit and scope of the invention.

We claim:

1. A hybrid, copolymeric magnetic-resonance-imaging contrast agent comprising:
   at least one chelating unit monomer;
   at least one free radical monomer linked to said at least one chelating unit monomer; and
   at least one paramagnetic ion combined with at least one of said at least one chelating unit monomer;
   wherein said chelating unit monomer is a polynitrilo chelating agent and said free radical monomer is a nitroxide.

2. The contrast agent of claim 1, having the following structure:

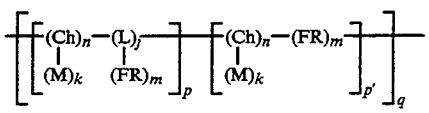

wherein Ch is a polynitrilo chelating unit monomer, L is a linker monomer, FR is a nitroxide free radical monomer, and M is a paramagnetic ion;
wherein q=1 to 10,000;
wherein, within each of the q polymeric groups

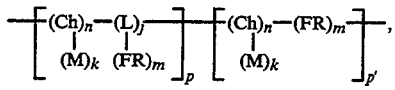

independently, p=0 to 10,000 and p'=0 to 10,000;
wherein, within each of the p oligomeric groups

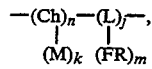

independently, n=0 to 10,000 and j=0 to 10,000;
for each group of paramagnetic ions

chelated by each of the n chelating unit monomers —Ch— in the p oligomeric groups, independently, k=0 to 2; and for each group of free radical monomers

linked to each of the j linker monomers —L— in the p oligomeric groups, independently, m=0 to 2; and
wherein, within each of the p' oligomeric groups

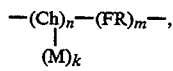

independently, n=0 to 10,000 and m=0 to 10,000; and for each group of paramagnetic ions

chelated by each of the n chelating unit monomers —Ch— in the p' oligomeric groups, independently, k=0 to 2.

3. The contrast agent of claim 1, wherein each polynitrilo chelating agent comprises at least one COOH, COOR$_1$, or COZ group; each R$_1$ being, independently, a C1–C20 substituted or unsubstituted, saturated or unsaturated, alkyl or cycloalkyl group or an anhydride; and each Z being, independently, Cl, Br, or I.

4. The contrast agent of claim 3, wherein at least one of said C1–C20 alkyl or cycloalkyl group is substituted with at least one moiety selected from the group of OH, NH$_2$, SH, COOH, and PO$_4$, or mixtures thereof.

5. The contrast agent of claim 3, wherein each R$_1$ is, independently, a polyhydroxy-substituted alkyl or cycloalkyl group.

6. The contrast agent of claim 5, wherein said polyhydroxy-substituted alkyl or cycloalkyl group is selected from the group consisting of sugar alcohols, monosaccharides, polysaccharides, and synthetic polymers, or mixtures thereof.

7. The contrast agent of claim 1, wherein each polynitrilo chelating unit monomer consists, independently, of a chelating agent selected from the group consisting of ethylenediamine tetraacetic acid; diethylenetriamine pentaacetic acid; 1,5-di-methoxyethylene-iminocarbonyl-methylene-1,3,5-tricarboxymethylene-1,3,5,-triazapentane; 1,5-di-α,-dihydroxypropeneimino-carbonylmethylene-1,3,5-tricarboxymethylene-1,3,5-triazapentane; 1,4,7,10-tetraazacyclododecane-1,4,7,10-tetraacetic acid; 1,4,7,10-tetraazacyclododecane-N,N',N''-triacetic acid; 3,6,9-triaza-12-oxa-3,6,9-tricarboxymethylene-10-carboxy-13-phenyl-tridecanoic acid; hydroxybenzyl-ethylenediamine diacetic acid; N,N'-bis(pyridoxyl-5-phosphate)ethylenediamine-N,N'-diacetic acid; 1,4,7-triazacyclononane-N,N',N''-triacetic acid; 1-oxa-4,7,10-triazacyclododecane-triacetic acid; 1,4,8,11-tetraazacyclotetradecane-N,N',N'',N'''-tetraacetic acid; triethylenetetraamine hexaacetic acid; 1,2-diaminocyclohexane-N,N,N',N'-tetraacetic acid; and anhydrides thereof.

8. The contrast agent of claim 1, wherein each free radical monomer is selected from the group consisting of heterocyclic nitroxide monomers and non-heterocyclic nitroxide monomers.

9. The contrast agent of claim 8, wherein said heterocyclic nitroxide monomers have the following general structure:

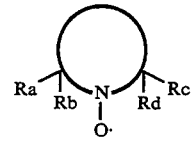

wherein
a five member ring is pyrrolidine, oxazolidine, imidazolidine, or thiazolidine;
a six member ring is piperidine; and
each of Ra, Rb, Rc and Rd is, independently, a C1–C20 alkyl or cycloalkyl group, said alkyl or cycloalkyl group being interrupted or terminated with OH, SH, NH$_2$, NHR$_1$, COOH, COOR$_1$, NCS, COCHCH$_2$, or COZ, each R$_1$ being, independently, a C1–C20 substituted or unsubstituted alkyl or cycloalkyl group or an anhydride, and each Z being, independently, Cl, Br, or I.

10. The contrast agent of claim 8, wherein said non-heterocyclic nitroxide monomers are selected from the group consisting of diphenylnitroxide and di-tert-butyl nitroxide.

11. The contrast agent of claim 1, wherein each nitroxide free radical monomer is selected from the group consisting of 2,2,6,6-tetramethylpiperidine-1-oxyl; 2,2,4,4-tetramethyl-pyrrolidine-1-oxyl; 2,2,4,4-tetramethyl-imidazolidine-3-oxyl; 2,2,4,4-tetramethyl-1,3-thiazolidine-3-oxyl; 2,2,4,4-tetramethyl-1,3-oxazolidine-3-oxyl; 2,2,6,6-tetramethylpyrimidine-1-oxyl; diphenylnitroxide; and di-tert-butylnitroxide; and wherein each nitroxide may have one or more OH, SH, NH$_2$, NHR$_1$, COOH, COOR$_1$, NCS, COCHCH$_2$, or COZ, each R$_1$ being, independently, a C1–C20 substituted or unsubstituted alkyl or cycloalkyl group or an anhydride, and each Z being, independently, Cl, Br, or I.

12. The contrast agent of claim 1, wherein each nitroxide free radical monomer is a monofunctionalized compound selected from the group consisting of 1-oxyl-2,2,6,6-tetramethyl-4-piperidinyl acrylate; 4-(iodomethylenecarbonylimino)-2,2,6,6-tetramethyl-piperdinyl-1-oxy; 4-(bromomethylenecarbonylimino)-2,2,6,6-tetramethyl-piperidinyl-1-oxy; 3-carboxy-2,2,5,5-tetramethylpyrrolidinyl-1-oxy; 3-chlorocarbonyl-2,2,5,5-tetramethylpyrrolidinyl-1-oxy; 3-aminomethylene-2,2,5,5-tetramethylpyrrolidinyl-1-oxy; 3-hydroxymethylene-2,2,5,5-tetramethylpyrrolidinyl-1-oxy; 3-hydroxy-2,2,5,5-tetramethylpyrrolidine-1-oxyl; 3-chloroformyl-2,2,5,5-tetramethylpyrrolidine-1-oxyl; 4-amino-2,2,6,6-tetramethylpiperidine-1-oxyl; 4-hydroxy-2,2,6,6-tetramethylpiperidine-1-oxyl; and 3-thiocabamoylmethylene-2,2,5,5-tetramethylpyrrolidinyl-1-oxy.

13. The contrast agent of claim 1, wherein each nitroxide free radical monomer is a difunctionalized compound selected from the group consisting of cis-1-oxyl-2,2,5,5-tetramethylpyrrolidine; trans-1-oxyl-2,2,5,5-tetramethylpyrrolidine; 3-amino-4-aminomethylene-2,2,5,5-tetramethylpyrrolidine; cis-2,5-dimethyl-2(aminomethyl)-5-(2-carboxyethyl)-tetrahydropyrrole-1-oxyl; cis-2,5-dimethyl-2-(hydroxymethyl)-5-(methoxycarbonylmethyl)-tetrahydropyrrole-1-oxyl; cis-2,5-dimethyl-2-(hydroxymethyl)-5-(2-hydroxyhexyl)-tetrahydropyrrole-1-oxyl; cis-2,5-dimethyl-2,5-bis(3-hydroxypropyl)-pyrrolidinyl-1-oxy; trans-2,5-dimethyl-2,5-bis(3-hydroxypropyl)-pyrrolidinyl-1-oxy; trans-2,5-dimethyl-2,5-bis(2-carboxyethyl)-pyrrolidinyl-1-oxy; cis-2,5-dimethyl-2,5-bis(2-hydroxy-5-methylphenyl)-tetrahydroxypyrrol-1-oxy; 3-amino-4-carboxy-2,2,5,5-tetramethylpyrrolidinyl-1-oxy; 2,5-di-tertbutyl-3,4-diethyloxycarbonyl-pyrrol-1-oxyl; and 1,4-bis(4-hydroxy-2,2,6,6-tetramethyl-1-oxyl-4-piperidyl)-butane.

14. The contrast agent of claim 1, wherein each paramagnetic ion is selected from the group consisting of transition and lanthanide elements.

15. The contrast agent of claim 1, wherein each paramagnetic ion is selected from the group consisting of Gd(III), Mn(II), Cu(II), Cr(III), Fe(II), Fe(III), Co(II), Er(II), Ni(II), Eu(III), Dy(III), Yb(III), and Ho(III).

16. The contrast agent of claim 1, wherein each paramagnetic ion is selected from the group consisting of Gd(III), Mn(II) and Fe(III).

17. The contrast agent of claim 2, wherein each linker monomer has the following general structure:

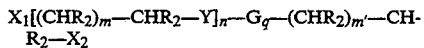

wherein
each $R_2$ is, independently, a C1–C20 substituted or unsubstituted, saturated or unsaturated, alkyl or cycloalkyl group;
$X_1$ and $X_2$ are, independently, OH, $NH_2$, $NHR_1$, COOH, $COOR_1$, SH, Z or NCS;
Y is O, NH, $NR_1$, S or CO;
each $R_1$ is, independently, a C1–C20 substituted or unsubstituted alkyl or cycloalkyl group or an anhydride;
each Z is, independently, Cl, Br, or I;
G is a C1–C20 substituted or unsubstituted alkyl or cycloalkyl group, a saccharide, a peptide or a polysulfide; and
m, m', n, and q are, independently, 0 to 10,000.

18. The contrast agent of claim 17, wherein each linker monomer is, independently, a polyamino linker monomer selected from the group consisting of 1,2-diaminoethane, 13-diaminopropane, 1,4-diaminobutane, 1,5-diamino-3-(2-aminoethyl)-pentane, N,N'-dimethyl-1,2-diaminoethane, N,N'-dimethyl-1,3-diaminopropane, 2-hydroxy-1,3-diaminopropane, 2-amino-1,3-diaminopropane, 2,3-diamino-1,4-butanediol, 1,4-diamino-2,3-butane diol, 1,4-diaminocyclohexane, 1,4-phenylenediamine, 1,1,1-tris(aminomethyl)ethane, 2,2',2''-tris-aminoethylamine, tris(aminomethylene)methane, diethylenetriamine, triethylenetetraamine, 1,3,5-triaminocyclohexane, and 1,3,5-triaminobenzene.

19. The contrast agent of claim 17, wherein each linker monomer is a polyhydroxy linker monomer selected from the group consisting of 2,2-dimethyl-1,3-propanediol, tris-(2-hydroxyethyl)amine, 1,1,1-tris-(hyroxymethylene)ethane, glycerine, erythritol, sugar alcohols, polyethyleneglycol, w-amino-polyethyleneglycol, N-substituted-w-aminopolyethyleneglycol, w-thiol-polyethyleneglycol, polysulfide-blocked polyethyleneglycol, and polyethylene-imine.

20. The contrast agent of claim 17, wherein each linker monomer is selected from the group consisting of ethylenedioxydiethylamine, N,N'-bis-dihydroxypropylethylenedioxydiethylamine, and ethylenedioxydiethylmercaptane.

21. The contrast agent of claim 2, wherein each polynitrilo chelating unit monomer comprises at least one COOH, $COOR_1$, or COZ group; each $R_1$ being, independently, a C1–C20 substituted or unsubstituted, saturated or unsaturated, alkyl or cycloalkyl group or an anhydride; and each Z being, independently, Cl, Br, or I.

22. The contrast agent of claim 21, wherein at least one of said C1–C20 alkyl or cycloalkyl group is substituted with at least one moiety selected from the group of OH, $NH_2$, SH, COOH, and $PO_4$, or mixtures thereof.

23. The contrast agent of claim 21, wherein each $R_1$ is, independently, a polyhydroxy-substituted alkyl or cycloalkyl group.

24. The contrast agent of claim 23, wherein said polyhydroxy-substituted alkyl or cycloalkyl group is selected from the group consisting of sugar alcohols, monosaccharides, polysaccharides, and synthetic polymers.

25. The contrast agent of claim 2, wherein each polynitrilo chelating unit monomer consists, independently, of a chelating agent selected from the group consisting of ethylenediamine tetraacetic acid; diethylenetriamine pentaacetic acid; 1,5-di-methoxyethylene-iminocarbonyl-methylene-1,3,5-tricarboxymethylene-1,3,5,-triazapentane; 1,5-di-α,-dihydroxypropeneiminocarbonyl-methylene-1,3,5-tricarboxymethylene-1,3,5-triazapentane; 1,4,7,10-tetraazacyclododecane-1,4,7,10-tetraacetic acid; 1,4,7,10-tetraazacyclododecane-N,N',N''-triacetic acid; 3,6,9-triaza-12-oxa-3,6,9-tricarboxymethylene-10-carboxy-13-phenyl-tridecanoic acid; hydroxybenzyl-ethylenediamine diacetic acid; N,N'-bis(pyridoxyl-5-phosphate)ethylenediamine-N,N'-diacetic acid; 1,4,7-triazacyclononane-N,N',N''-triacetic acid; 1-oxa-4,7,10-triazacyclododecane-triacetic acid; 1,4,8,11-tetraazacyclotetradecane-N,N',N'',N'''-tetraacetic acid; triethylenetetraamine hexaacetic acid; 1,2-diaminocyclohexane-N,N,N',N'-tetraacetic acid; and anhydrides thereof.

26. The contrast agent of claim 2, wherein each free radical monomer, independently, is selected from the group consisting of heterocyclic nitroxide monomers and non-heterocyclic nitroxide monomers.

27. The contrast agent of claim 26, wherein said heterocyclic nitroxide monomers have the following general structure:

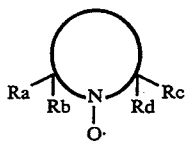

wherein
  a five member ring is pyrrolidine, oxazolidine, imidazolidine, or thiazolidine;
  a six member ring is piperidine; and
  each of Ra, Rb, Rc and Rd is, independently, a C1–C20 alkyl or cycloalkyl group, said alkyl or cycloalkyl group being interrupted or terminated with OH, SH, $NH_2$, $NHR_1$, COOH, $COOR_1$, NCS, $COCHCH_2$, or COZ, each $R_1$ being, independently, a C1–C20 substituted or unsubstituted alkyl or cycloalkyl group or an anhydride, and each Z being, independently, Cl, Br, or I.

28. The contrast agent of claim 26, wherein said non-heterocyclic nitroxide monomers are selected from the group consisting of diphenylnitroxide and di-tert-butyl nitroxide.

29. The contrast agent of claim 2, wherein each nitroxide free radical monomer is, independently, selected from the group consisting of 2,2,6,6-tetramethylpiperidine-1-oxyl; 2,2,4,4-tetramethyl-pyrrolidine-1-oxyl; 2,2,4,4-tetramethylimidazolidine-3-oxyl; 2,2,4,4-tetramethyl-1,3-thiazolidine-3-oxyl; 2,2,4,4-tetramethyl-1,3-oxazolidine-3-oxyl; 2,2,6,6-tetramethylpyrimidine-1-oxyl; diphenyl-nitroxide; and di-tertbutylnitroxide; and wherein each nitroxide may have one or more OH, SH, $NH_2$, $NHR_1$, COOH, $COOR_1$, NCS, $COCHCH_2$, or COZ, each $R_1$ being, independently, a C1–C20 substituted or unsubstituted alkyl or cycloalkyl group or an anhydride, and each Z being, independently, Cl, Br, or I.

30. The contrast agent of claim 2, wherein each nitroxide free radical monomer is, independently, a mono-functionalized compound selected from the group consisting of 1-oxyl-2,2,6,6-tetramethyl-4-piperidinyl acrylate; 4-(iodomethylenecarbonylimino)-2,2,6,6-tetramethyl-piperdinyl-1-oxy; 4-(bromomethylenecarbonylimino)-2,2,6,6-tetramethyl-piperidinyl-1-oxy; 3-carboxy-2,2,5,5-tetramethylpyrrolidinyl-1-oxy; 3-chlorocarbonyl-2,2,5,5-tetramethylpyrrolidinyl-1-oxy; 3-aminomethylene-2,2,5,5-tetramethylpyrrolidinyl-1-oxy; 3-hydroxymethylene-2,2,5,5-tetramethylpyrrolidinyl-1-oxyl; 3-hydroxy-2,2,5,5-tetramethylpyrrolidine-1-oxyl; 3-chloroformyl-2,2,5,5-tetramethylpyrrolidine-1-oxyl; 4-amino-2,2,6,6-tetramethylpiperidine-1-oxyl; 4-hydroxy-2,2,6,6-tetramethylpiperidine-1-oxyl; and 3-thiocabamoylmethylene-2,2,5,5-tetramethylpyrrolidinyl-1-oxy.

31. The contrast agent of claim 2, wherein each nitroxide free radical monomer is, independently, a di-functionalized compound selected from the group consisting of cis-1-oxyl-2,2,5,5-tetramethylpyrrolidine; trans-1-oxyl-2,2,5,5-tetramethylpyrrolidine; 3-amino-4-aminomethylene-2,2,5,5-tetramethylpyrrolidine; cis-2,5-dimethyl-2(aminomethyl)-5-(2-carboxyethyl)-tetrahydropyrrole-1-oxyl; cis-2,5-dimethyl-2-(hydroxymethyl)-5-(methoxycarbonylmethyl)-tetrahydropyrrole-1-oxyl; cis-2,5-dimethyl-2-(hydroxymethyl)-5-(2-hydroxyhexyl)-tetrahydropyrrole-1-oxyl; cis-2,5-dimethyl-2,5-bis(3-hydroxypropyl)-pyrrolidinyl-1-oxy; trans-2,5-dimethyl-2,5-bis(3-hydroxypropyl)-pyrrolidinyl-1-oxy; trans-2,5-dimethyl-2,5-bis(2-carboxyethyl)-pyrrolidinyl-1-oxy; cis-2,5-dimethyl-2,5-bis(2-hydroxy-5-methylphenyl)-tetrahydroxypyrrol-1-oxy; 3-amino-4-carboxy-2,2,5,5-tetramethylpyrrolidinyl-1-oxy; 2,5-di-tert-butyl-3,4-diethyloxycarbonyl-pyrrol-1-oxyl; and 1,4-bis(4-hydroxy-2,2,6,6-tetramethyl-1-oxyl-4-piperidyl)-butane.

32. The contrast agent of claim 2, wherein each paramagnetic ion is selected from the group consisting of transition and lanthanide elements.

33. The contrast agent of claim 2, wherein each paramagnetic ion is selected from the group consisting of Gd(III), Mn(II), Cu(II), Cr(III), Fe(II), Fe(III), Co(II), Er(II), Ni(II), Eu(III), Dy(III), Yb(III), and Ho(III).

34. The contrast agent of claim 2, wherein each paramagnetic ion is selected from the group consisting of Gd(III), Mn(II) and Fe(III).

35. The contrast agent of claim 1, having the following structure:

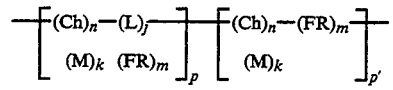

wherein Ch is a polynitrilo chelating unit monomer, L is a linker monomer, FR is a nitroxide free radical monomer, and M is a paramagnetic ion;
wherein, independently, p=1 to 10,000 and p'=1 to 10,000;
wherein, within each of the p oligomeric groups

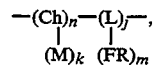

independently, n=0 to 10,000 and j=0 to 10,000; for each group of paramagnetic ions

chelated by each of the n chelating unit monomers —Ch— in each of the p oligomeric groups, independently, k=0 to 2; and for each group of free radical monomers

linked to each of the j linker monomers —L— in each of the oligomeric groups, independently, m=0 to 2; and
wherein, within each of the p' oligomeric groups

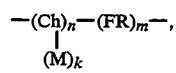

independently, n=0 to 10,000 and m=0 to 10,000; and for each group of paramagnetic ions

chelated by each of the n chelating unit monomers —Ch— in each of the p' oligomeric groups, independently, k=0 to 2.

36. The contrast agent of claim 35, wherein each linker monomer has the following general structure:

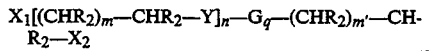

wherein
each $R_2$ is, independently, a C1–C20 substituted or unsubstituted, saturated or unsaturated, alkyl or cycloalkyl group;
$X_1$ and $X_2$ are, independently, OH, $NH_2$, $NHR_1$, COOH, $COOR_1$, SH, Z or NCS;
Y is O, NH, $NR_1$, S or CO;
each $R_1$ is, independently, a C1–C20 substituted or unsubstituted alkyl or cycloalkyl group or an anhydride;
each Z is, independently, Cl, Br, or I;
G is a C1–C20 substituted or unsubstituted alkyl or cycloalkyl group, a saccharide, a peptide or a polysulfide; and
m, m', n, and q are, independently, 0 to 10,000.

37. The contrast agent of claim 36, wherein each linker monomer is, independently, a polyamino linker monomer selected from the group consisting of 1,2-diaminoethane, 13-diaminopropane, 1,4-diaminobutane, 1,5-diamino-3-(2-aminoethyl)-pentane, N,N'-dimethyl-1,2-diaminoethane, N,N'-dimethyl-1,3-diaminopropane, 2-hydroxy-1,3-diaminopropane, 2-amino-1,3-diaminopropane, 2,3-diamino-1,4-butanediol, 1,4-diamino-2,3-butane diol, 1,4-diaminocyclohexane, 1,4-phenylenediamine, 1,1,1-tris-(aminomethyl)ethane, 2,2',2''-trisaminoethylamine, tris-(aminomethylene)methane, diethylenetriamine, triethylenetetraamine, 1,3,5-triaminocyclohexane, and 1,3,5-triaminobenzene.

38. The contrast agent of claim 36, wherein each linker monomer is a polyhydroxy linker monomer selected from the group consisting of 2,2-dimethyl-1,3-propanediol, tris-(2-hydroxyethyl)amine, 1,1,1-tris-(hyroxymethylene)ethane, glycerine, erythritol, sugar alcohols, polyethyleneglycol, w-amino-polyethyleneglycol, N-substituted-w-aminopolyethyleneglycol, w-thiol-polyethyleneglycol, polysulfide-blocked polyethyleneglycol, and polyethylene-imine.

39. The contrast agent of claim 36, wherein each linker monomer is selected from the group consisting of ethylenedioxydiethylamine, N,N'-bis-dihydroxypropylethylenedioxydiethylamine, and ethylenedioxydiethylmercaptane.

40. The contrast agent of claim 35, wherein each polynitrilo chelating unit monomer comprises at least one COOH, $COOR_1$, or COZ group; each $R_1$ being independently, a C1–C20 substituted or unsubstituted, saturated or unsaturated, alkyl or cycloalkyl group or an anhydride; and each Z being, independently, Cl, Br, or I.

41. The contrast agent of claim 40, wherein at least one of said C1–C20 alkyl or cycloalkyl group is substituted with at least one moiety selected from the group of OH, $NH_2$, SH, COOH, and $PO_4$, or mixtures thereof.

42. The contrast agent of claim 40, wherein each $R_1$ is, independently, a polyhydroxy-substituted alkyl or cycloalkyl group.

43. The contrast agent of claim 42, wherein said polyhydroxy-substituted alkyl or cycloalkyl group is selected from the group consisting of sugar alcohols, monosaccharides, polysaccharides, and synthetic polymers.

44. The contrast agent of claim 35, wherein each polynitrilo chelating unit monomer consists, independently, of a chelating agent selected from the group consisting of ethylenediamine tetraacetic acid; diethylenetriamine pentaacetic acid; 1,5-di-methoxyethyleneiminocarbonyl-methylene-1,3,5-tricarboxymethylene-1,3,5,-triazapentane; 1,5-di-α,-dihydroxypropeneiminocarbonyl-methylene-1,3,5-tricarboxymethylene-1,3,5-triazapentane; 1,4,7,10-tetraazacyclododecane-1,4,7,10-tetraacetic acid; 1,4,7,10-tetraazacyclododecane-N,N',N''-triacetic acid; 3,6,9-triaza-12-oxa-3,6,9-tricarboxymethylene-10-carboxy-13-phenyl-tridecanoic acid; hydroxybenzyl-ethylenediamine diacetic acid; N,N'-bis(pyridoxyl-5-phosphate)ethylenediamine-N,N'-diacetic acid; 1,4,7-triazacyclononane-N,N',N''-triacetic acid; 1-oxa-4,7,10-triazacyclododecane-triacetic acid; 1,4,8,11-tetraazacyclotetradecane-N,N',N'',N'''-tetraacetic acid; triethylenetetraamine hexaacetic acid; 1,2-diaminocyclohexane-N,N,N',N'-tetraacetic acid; and anhydrides thereof.

45. The contrast agent of claim 35, wherein each free radical monomer, independently, is selected from the group consisting of heterocyclic nitroxide monomers and non-heterocyclic nitroxide monomers.

46. The contrast agent of claim 45, wherein said heterocyclic nitroxide monomers have the following general structure:

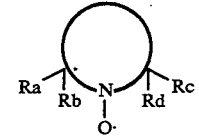

wherein
a five member ring is pyrrolidine, oxazolidine, imidazolidine, or thiazolidine;
a six member ring is piperidine; and
each of Ra, Rb, Rc and Rd is, independently, a C1–C20 alkyl or cycloalkyl group, said alkyl or cycloalkyl group being interrupted or terminated with OH, SH, $NH_2$, $NHR_1$, COOH, $COOR_1$, NCS, $COCHCH_2$, or COZ, each $R_1$ being, independently, a C1–C20 substituted or unsubstituted alkyl or cycloalkyl group or an anhydride, and each Z being, independently, Cl, Br, or I.

47. The contrast agent of claim 45, wherein said non-heterocyclic nitroxide monomers are selected from the group consisting of diphenylnitroxide and di-tert-butyl nitroxide.

48. The contrast agent of claim 35, wherein each nitroxide free radical monomer is, independently, selected from the group consisting of 2,2,6,6-tetramethyl-piperidine-1-oxyl; 2,2,4,4-tetramethyl-pyrrolidine-1-oxyl; 2,2,4,4-tetramethylimidazolidine-3-oxyl; 2,2,4,4-tetramethyl-1,3-thiazolidine-3-oxyl; 2,2,4,4-tetramethyl-1,3-oxazolidine-3-oxyl; 2,2,6,6-tetramethylpyrimidine-1-oxyl; diphenyl-nitroxide; and di-tertbutylnitroxide;

and wherein each nitroxide may have one or more OH, SH, NH$_2$, NHR$_1$, COOH, COOR$_1$, NCS, COCHCH$_2$, or COZ, each R$_1$ being, independently, a C1–C20 substituted or unsubstituted alkyl or cycloalkyl group or an anhydride, and each Z being, independently, Cl, Br, or I.

49. The contrast agent of claim 35, wherein each nitroxide free radical monomer is, independently, a monofunctionalized compound selected from the group consisting of 1-oxyl-2,2,6,6-tetramethyl-4-piperidinyl acrylate; 4-(iodomethylenecarbonylimino)-2,2,6,6-tetramethyl-piperdinyl-1-oxy; 4-(bromomethylenecarbonylimino)-2,2,6,6-tetramethyl-piperidinyl-1-oxy; 3-carboxy-2,2,5,5-tetramethylpyrrolidinyl-1-oxy; 3-chlorocarbonyl-2,2,5,5-tetramethylpyrrolidinyl-1-oxy; 3-aminomethylene-2,2,5,5-tetramethylpyrrolidinyl-1-oxy; 3-hydroxymethylene-2,2,5,5-tetramethylpyrrolidinyl-1-oxyl; 3-hydroxy-2,2,5,5-tetramethylpyrrolidine-1-oxyl; 3-chloroformyl-2,2,5,5-tetramethylpyrrolidine-1-oxyl; 4-amino-2,2,6,6-tetramethylpiperidine-1-oxyl; 4-hydroxy-2,2,6,6-tetramethylpiperidine-1-oxyl; and 3-thiocabamoylmethylene-2,2,5,5-tetramethylpyrrolidinyl-1-oxy.

50. The contrast agent of claim 35, wherein each nitroxide free radical monomer is, independently, a difunctionalized compound selected from the group consisting of cis-1-oxyl-2,2,5,5-tetramethylpyrrolidine; trans-1-oxyl-2,2,5,5-tetramethylpyrrolidine; 3-amino-4-aminomethylene-2,2,5,5-tetramethylpyrrolidine; cis-2,5-dimethyl-2(aminomethyl)-5-(2-carboxyethyl)-tetrahydropyrrole-1-oxyl; cis-2,5-dimethyl-2-(hydroxymethyl)-5-(methoxycarbonylmethyl)-tetrahydropyrrole-1-oxyl; cis-2,5-dimethyl-2-(hydroxymethyl)-5-(2-hydroxyhexyl)-tetrahydropyrrole-1-oxyl; cis-2,5-dimethyl-2,5-bis(3-hydroxypropyl)-pyrrolidinyl-1-oxy; trans-2,5-dimethyl-2,5-bis(3-hydroxypropyl)-pyrrolidinyl-1-oxy; trans-2,5-dimethyl-2,5-bis(2-carboxyethyl)-pyrrolidinyl-1-oxy; cis-2,5-dimethyl-2,5-bis(2-hydroxy-5-methylphenyl)-tetrahydroxypyrrol-1-oxy; 3-amino-4-carboxy-2,2,5,5-tetramethylpyrrolidinyl-1-oxy; 2,5-di-tert-butyl-3,4-diethyloxycarbonyl-pyrrol-1-oxyl; and 1,4-bis(4-hydroxy-2,2,6,6-tetramethyl-1-oxyl-4-piperidyl)-butane.

51. The contrast agent of claim 35, wherein each paramagnetic ion is selected from the group consisting of transition and lanthanide elements.

52. The contrast agent of claim 35, wherein each paramagnetic ion is selected from the group consisting of Gd(III), Mn(II), Cu(II), Cr(III), Fe(II), Fe(III), Co(II), Er(II), Ni(II), Eu(III), Dy(III), Yb(III), and Ho(III).

53. The contrast agent of claim 35, wherein each paramagnetic ion is selected from the group consisting of Gd(III), Mn(II) and Fe(III).

54. The contrast agent of claim 1, having the following structure:

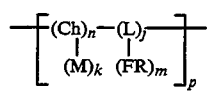

wherein Ch is a polynitrilo chelating unit monomer, L is a linker monomer, FR is a nitroxide free radical monomer, and M is a paramagnetic ion;
wherein p=1 to 10,000; and
wherein, within each of the p oligomeric groups

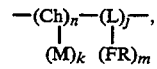

independently, n=0 to 10,000 and j=0 to 10,000; for each group of paramagnetic ions

chelated by each of the n chelating unit monomers —Ch— in each of the p oligomeric groups, independently, k=0 to 2; and for each group of free radical monomers

linked to each of the j linker monomers —L— in each of the oligomeric groups, independently, m=0 to 2.

55. The contrast agent of claim 54, wherein each linker monomer has the following general structure:

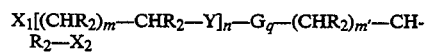

wherein
each R$_1$ is, independently, a C1–C20 substituted or unsubstituted, saturated or unsaturated, alkyl or cycloalkyl group;
X$_1$ and X$_2$ are, independently, OH, NH$_2$, NHR$_1$, COOH, COOR$_1$, SH, Z or NCS;
Y is O, NH, NR$_1$, S or CO;
each R$_1$ is, independently, a C1–C20 substituted or unsubstituted alkyl or cycloalkyl group or an anhydride;
each Z is, independently, Cl, Br, or I;
G is a C1–C20 substituted or unsubstituted alkyl or cycloalkyl group, a saccharide, a peptide or a polysulfide; and
m, m', n, and q are, independently, 0 to 10,000.

56. The contrast agent of claim 55, wherein each linker monomer is, independently, a polyamino linker monomer selected from the group consisting of 1,2-diaminoethane, 13-diaminopropane, 1,4-diaminobutane, 1,5-diamino-3-(2-aminoethyl)-pentane, N,N'-dimethyl-1,2-diaminoethane, N,N'-dimethyl-1,3-diaminopropane, 2-hydroxy-1,3-diaminopropane, 2-amino-1,3-diaminopropane, 2,3-diamino-1,4-butanediol, 1,4-diamino-2,3-butane diol, 1,4-diaminocyclohexane, 1,4-phenylenediamine, 1,1,1-tris-(aminomethyl)ethane, 2,2',2''-trisaminoethylamine, tris-(aminomethylene)methane, diethylenetriamine, triethylenetetraamine, 1,3,5-triaminocyclohexane, and 1,3,5-triaminobenzene.

57. The contrast agent of claim 55, wherein each linker monomer is a polyhydroxy linker monomer selected from the group consisting of 2,2-dimethyl-1,3-propanediol, tris-(2-hydroxyethyl)amine, 1,1,1-tris-(hyroxymethylene)ethane, glycerine, erythritol, sugar alcohols, polyethyleneglycol, w-amino-polyethyleneglycol, N-substituted-w-aminopolyethyleneglycol, w-thiol-polyethyleneglycol, polysulfide-blocked polyethyleneglycol, and polyethylene-imine.

58. The contrast agent of claim 55, wherein each linker monomer is selected from the group consisting of ethylenedioxydiethylamine, N,N'-bis-dihydroxy-propylethylenedioxydiethylamine, and ethylenedioxydiethylmercaptane.

59. The contrast agent of claim 54, wherein each polynitrilo chelating unit monomer comprises at least one COOH, COOR$_1$, or COZ group; each R$_1$ being, independently, a C1–C20 substituted or unsubstituted, saturated or unsaturated, alkyl or cycloalkyl group or an anhydride; and each Z being, independently, Cl, Br, or I.

60. The contrast agent of claim 59, wherein at least one of said C1–C20 alkyl or cycloalkyl group is substituted with at least one moiety selected from the group of OH, NH$_2$, SH, COOH, and PO$_4$, or mixtures thereof.

61. The contrast agent of claim 59, wherein each R$_1$ is, independently, a polyhydroxy-substituted alkyl or cycloalkyl group.

62. The contrast agent of claim 61, wherein said polyhydroxy-substituted alkyl or cycloalkyl group is selected from the group consisting of sugar alcohols, monosaccharides, polysaccharides, and synthetic polymers.

63. The contrast agent of claim 54, wherein each polynitrilo chelating unit monomer consists, independently, of a chelating agent selected from the group consisting of ethylenediamine tetraacetic acid; diethylenetriamine pentaacetic acid; 1,5-di-methoxyethylene-iminocarbonyl-methylene-1,3,5-tricarboxymethylene-1,3,5,-triazapentane; 1,5-di-α,-dihydroxypropeneiminocarbonyl-methylene-1,3,5-tricarboxymethylene-1,3,5-triazapentane; 1,4,7,10-tetraazacyclododecane-1,4,7,10-tetraacetic acid; 1,4,7,10-tetraazacyclododecane-N,N',N"-triacetic acid; 3,6,9-triaza-12-oxa-3,6,9-tricarboxymethylene-10-carboxy-13-phenyl-tridecanoic acid; hydroxybenzyl-ethylenediamine diacetic acid; N,N'-bis(pyridoxyl-5-phosphate)ethylenediamine-N,N'-diacetic acid; 1,4,7-triazacyclononane-N,N',N"-triacetic acid; 1-oxa-4,7,10-triazacyclododecane-triacetic acid; 1,4,8,11-tetraazacyclotetradecane-N,N',N",N'''-tetraacetic acid; triethylenetetraamine hexaacetic acid; 1,2-diaminocyclohexane-N,N,N',N'-tetraacetic acid; and anhydrides thereof.

64. The contrast agent of claim 54, wherein each free radical monomer, independently, is selected from the group consisting of heterocyclic nitroxide monomers and non-heterocyclic nitroxide monomers.

65. The contrast agent of claim 64, wherein said heterocyclic nitroxide monomers have the following general structure:

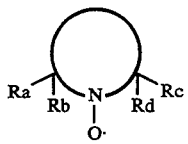

wherein
a five member ring is pyrrolidine, oxazolidine, imidazolidine, or thiazolidine;
a six member ring is piperidine; and
each of Ra, Rb, Rc and Rd is, independently, a C1–C20 alkyl or cycloalkyl group, said alkyl or cycloalkyl group being interrupted or terminated with OH, SH, NH$_2$, NHR$_1$, COOH, COOR$_1$, NCS, COCHCH$_2$, or COZ, each R$_1$ being, independently, a C1–C20 substituted or unsubstituted alkyl or cycloalkyl group or an anhydride, and each Z being, independently, Cl, Br, or I.

66. The contrast agent of claim 64, wherein said non-heterocyclic nitroxide monomers are selected from the group consisting of diphenylnitroxide and di-tert-butyl nitroxide.

67. The contrast agent of claim 54, wherein each nitroxide free radical monomer is, independently, selected from the group consisting of 2,2,6,6-tetramethyl-piperidine-1-oxyl; 2,2,4,4-tetramethyl-pyrrolidine-1-oxyl; 2,2,4,4-tetramethylimidazolidine-3-oxyl; 2,2,4,4-tetramethyl-1,3-thiazolidine-3-oxyl; 2,2,4,4-tetramethyl-1,3-oxazolidine-3-oxyl; 2,2,6,6-tetramethylpyrimidine-1-oxyl; diphenyl-nitroxide; and di-tertbutylnitroxide; and wherein each nitroxide may have one or more OH, SH, NH$_2$, NHR$_1$, COOH, COOR$_1$, NCS, COCHCH$_2$, or COZ, each R$_1$ being, independently, a C1–C20 substituted or unsubstituted alkyl or cycloalkyl group or an anhydride, and each Z being, independently, Cl, Br, or I.

68. The contrast agent of claim 54, wherein each nitroxide free radical monomer is, independently, a monofunctionalized compound selected from the group consisting of 1-oxyl-2,2,6,6-tetramethyl-4-piperidinyl acrylate; 4-(iodomethylenecarbonylimino)-2,2,6,6-tetramethyl-piperdinyl-1-oxy; 4-(bromomethylenecarbonylimino)-2,2,6,6-tetramethyl-piperidinyl-1-oxy; 3-carboxy-2,2,5,5-tetramethylpyrrolidinyl-1-oxy; 3-chlorocarbonyl-2,2,5,5-tetramethylpyrrolidinyl-1-oxy; 3-aminomethylene-2,2,5,5-tetramethylpyrrolidinyl-1-oxy; 3-hydroxymethylene-2,2,5,5-tetramethylpyrrolidinyl-1-oxyl; 3-hydroxy-2,2,5,5-tetramethylpyrrolidine-1-oxyl; 3-chloroformyl-2,2,5,5-tetramethylpyrrolidine-1-oxyl; 4-amino-2,2,6,6-tetramethylpiperidine-1-oxyl; 4-hydroxy-2,2,6,6-tetramethylpiperidine-1-oxyl; and 3-thiocabamoylmethylene-2,2,5,5-tetramethylpyrrolidinyl-1-oxy.

69. The contrast agent of claim 54, wherein each nitroxide free radical monomer is, independently, a difunctionalized compound selected from the group consisting of cis-1-oxyl-2,2,5,5-tetramethylpyrrolidine; trans-1-oxyl-2,2,5,5-tetramethylpyrrolidine; 3-amino-4-aminomethylene-2,2,5,5-tetramethylpyrrolidine; cis-2,5-dimethyl-2(aminomethyl)-5-(2-carboxyethyl)-tetrahydropyrrole-1-oxyl; cis-2,5-dimethyl-2-(hydroxymethyl)-5-(methoxycarbonylmethyl)-tetrahydropyrrole-1-oxyl; cis-2,5-dimethyl-2-(hydroxymethyl)-5-(2-hydroxyhexyl)-tetrahydropyrrole-1-oxyl; cis-2,5-dimethyl-2,5-bis(3-hydroxypropyl)-pyrrolidinyl-1-oxy; trans-2,5-dimethyl-2,5-bis(3-hydroxypropyl)-pyrrolidinyl-1-oxy; trans-2,5-dimethyl-2,5-bis(2-carboxyethyl)-pyrrolidinyl-1-oxy; cis-2,5-dimethyl-2,5-bis(2-hydroxy-5-methylphenyl)-tetrahydroxypyrrol-1-oxy; 3-amino-4-carboxy-2,2,5,5-tetramethylpyrrolidinyl-1-oxy; 2,5-di-tert-butyl-3,4-diethyloxycarbonyl-pyrrol-1-oxyl; and 1,4-bis(4-hydroxy-2,2,6,6-tetramethyl-1-oxyl-4-piperidyl)-butane.

70. The contrast agent of claim 54, wherein each paramagnetic ion is selected from the group consisting of transition and lanthanide elements.

71. The contrast agent of claim 54, wherein each paramagnetic ion is selected from the group consisting of Gd(III), Mn(II), Cu(II), Cr(III), Fe(II), Fe(III), Co(II), Er(II), Ni(II), Eu(III), Dy(III), Yb(III), and Ho(III).

72. The contrast agent of claim 54, wherein each paramagnetic ion is selected from the group consisting of Gd(III), Mn(II) and Fe(III).

73. The contrast agent of claim 1, having the following structure:

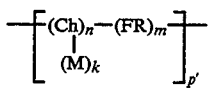

wherein Ch is a polynitrilo chelating unit monomer, FR is a nitroxide free radical monomer, and M is a paramagnetic ion;
wherein p'=1 to 10,000; and
wherein, within each of the p' oligomeric groups

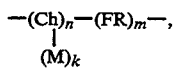

independently, n=0 to 10,000 and m=0 to 10,000; and for each group of paramagnetic ions

chelated by each of the n chelating unit monomers —Ch— in each of the p' oligomeric groups, independently, k=0 to 2.

74. The contrast agent of claim 73, wherein each polynitrilo chelating unit monomer comprises at least one COOH, COOR$_1$, or COZ group; each R$_1$ being, independently, a C1–C20 substituted or unsubstituted, saturated or unsaturated, alkyl or cycloalkyl group or an anhydride; and each Z being, independently, Cl, Br, or I.

75. The contrast agent of claim 74, wherein at least one of said C1–C20 alkyl or cycloalkyl group is substituted with at least one moiety selected from the group of OH, NH$_2$, SH, COOH, and PO$_4$, or mixtures thereof.

76. The contrast agent of claim 74, wherein each R$_1$ is, independently, a polyhydroxy-substituted alkyl or cycloalkyl group.

77. The contrast agent of claim 76, wherein said polyhydroxy-substituted alkyl or cycloalkyl group is selected from the group consisting of sugar alcohols, monosaccharides, polysaccharides, and synthetic polymers.

78. The contrast agent of claim 73, wherein each polynitrilo chelating unit monomer consists, independently, of a chelating agent selected from the group consisting of ethylenediamine tetraacetic acid; diethylenetriamine pentaacetic acid; 1,5-di-methoxyethylene-iminocarbonyl-methylene-1,3,5-tricarboxymethylene-1,3,5,-triazapentane; 1,5-di-α,dihydroxypropeneiminocarbonyl-methylene-1,3,5-tricarboxymethylene-1,3,5-triazapentane; 1,4,7,10-tetraazacyclododecane-1,4,7,10-tetraacetic acid; 1,4,7,10-tetraazacyclododecane-N,N',N''-triacetic acid; 3,6,9-triaza-12-oxa-3,6,9-tricarboxymethylene-10-carboxy-13-phenyl-tridecanoic acid; hydroxybenzyl-ethylenediamine diacetic acid; N,N'-bis(pyridoxyl-5-phosphate)ethylenediamine-N,N'-diacetic acid; 1,4,7-triazacyclononane-N,N',N''-triacetic acid; 1-oxa-4,7,10-triazacyclododecane-triacetic acid; 1,4,8,11-tetraazacyclotetradecane-N,N',N'',N'''-tetraacetic acid; triethylenetetraamine hexaacetic acid; 1,2-diaminocyclohexane-N,N,N',N'-tetraacetic acid; and anhydrides thereof.

79. The contrast agent of claim 73, wherein each free radical monomer, independently, is selected from the group consisting of heterocyclic nitroxide monomers and non-heterocyclic nitroxide monomers.

80. The contrast agent of claim 79, wherein said heterocyclic nitroxide monomers have the following general structure:

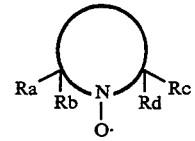

wherein
a five member ring is pyrrolidine, oxazolidine, imidazolidine, or thiazolidine;
a six member ring is piperidine; and
each of Ra, Rb, Rc and Rd is, independently, a C1–C20 alkyl or cycloalkyl group, said alkyl or cycloalkyl group being interrupted or terminated with OH, SH, NH$_2$, NHR$_1$, COOH, COOR$_1$, NCS, COCHCH$_2$, or COZ, each R$_1$ being, independently, a C1–C20 substituted or unsubstituted alkyl or cycloalkyl group or an anhydride, and each Z being, independently, Cl, Br, or I.

81. The contrast agent of claim 79, wherein said non-heterocyclic nitroxide monomers are selected from the group consisting of diphenylnitroxide and di-tert-butyl nitroxide.

82. The contrast agent of claim 73, wherein each nitroxide free radical monomer is, independently, selected from the group consisting of 2,2,6,6-tetramethyl-piperidine-1-oxyl; 2,2,4,4-tetramethyl-pyrrolidine-1-oxyl; 2,2,4,4-tetramethylimidazolidine-3-oxyl; 2,2,4,4-tetramethyl-1,3-thiazolidine-3-oxyl; 2,2,4,4-tetramethyl-1,3-oxazolidine-3-oxyl; 2,2,6,6-tetramethylpyrimidine-1-oxyl; diphenyl-nitroxide; and di-tertbutylnitroxide; and wherein each nitroxide may have one or more OH, SH, NH$_2$, NHR$_1$, COOH, COOR$_1$, NCS, COCHCH$_1$, or COZ, each R$_1$ being, independently, a C1–C20 substituted or unsubstituted alkyl or cycloalkyl group or an anhydride, and each Z being, independently, Cl, Br, or I.

83. The contrast agent of claim 73, wherein each nitroxide free radical monomer is, independently, a monofunctionalized compound selected from the group consisting of 1-oxyl-2,2,6,6-tetramethyl-4-piperidinyl acrylate; 4-(iodomethylenecarbonylimino)-2,2,6,6-tetramethyl-piperdinyl-1-oxy; 4-(bromomethylenecarbonylimino)-2,2,6,6-tetramethyl-piperidinyl-1-oxy; 3-carboxy-2,2,5,5-tetramethylpyrolidinyl-1-oxyl; 3-chlorocarbonyl-2,2,5,5-tetramethylpyrrolfdinyl-1-oxy; 3-aminomethylene-2,2,5,5-tetramethylpyrrolidinyl-1-oxy; 3-hydroxymethylene-2,2,5,5-tetramethylpyrrolidinyl-1-oxyl; 3-hydroxy-2,2,5,5-tetramethylpyrrolidine-1-oxyl; 3-chloroformyl-2,2,5,5-tetramethylpyrrolidine-1-oxyl; 4-amino-2,2,6,6-tetramethylpiperidine-1-oxyl; 4-hydroxy-2,2,6,6-tetramethylpiperidine-1-oxyl; and 3-thiocabamoylmethylene-2,2,5,5-tetramethylpyrrolidinyl-1-oxy.

84. The contrast agent of claim 73, wherein each nitroxide free radical monomer is, independently, a difunctionalized compound selected from the group consisting of cis-1-oxyl-2,2,5,5-tetramethylpyrrolidine; trans-1-oxyl-2,2,5,5-tetramethylpyrrolidine; 3-amino-4-aminomethylene-2,2,5,5-tetramethylpyrrolidine; cis-2,5-dimethyl-2(aminomethyl)-5-(2-carboxyethyl)-tetrahydropyrrole-1-oxyl; cis-2,5-dimethyl-2-(hydroxymethyl)-5-(methoxycarbonylmethyl)-tetrahydropyrrole-1-oxyl; cis-2,5-dimethyl-2-(hydroxymethyl)-5-(2-hydroxyhexyl)-tetrahydropyrrole-1-oxyl; cis-2,5-dimethyl-2,5-bis(3-hydroxypropyl)-pyrrolidinyl-1-oxy; trans-2,5-dimethyl-2,5-bis(3-hydroxypropyl)-pyrrolidinyl-1-oxy; trans-2,5-dimethyl-2,5-bis(2-carboxyethyl)-pyrrolidinyl-1-oxy; cis-2,5-dimethyl-2,5-bis(2-hydroxy-5-methylphenyl)-tetrahydroxypyrrol-1-oxy; 3-amino-4-carboxy-2,2,5,5-tetramethylpyrrolidinyl-1-oxy; 2,5-di-tert-butyl-3,4-diethyloxycarbonyl-pyrrol-1-oxyl; and 1,4-bis(4-hydroxy-2,2,6,6-tetramethyl-1-oxyl-4-piperidyl)-butane.

85. The contrast agent of claim 73, wherein each paramagnetic ion is selected from the group consisting of transition and lanthanide elements.

86. The contrast agent of claim 73, wherein each paramagnetic ion is selected from the group consisting of Gd(III), Mn(II), Cu(II), Cr(III), Fe(II), Fe(III), Co(II), Er(II), Ni(II), Eu(III), Dy(III), Yb(III), and Ho(III).

87. The contrast agent of claim 73, wherein each paramagnetic ion is selected from the group consisting of Gd(III), Mn(II) and Fe(III).

* * * * *